(12) United States Patent
Badawi

(10) Patent No.: US 9,724,230 B2
(45) Date of Patent: *Aug. 8, 2017

(54) DRY EYE TREATMENT APPARATUS AND METHODS

(75) Inventor: Paul Badawi, San Francisco, CA (US)

(73) Assignee: Sight Sciences, Inc., Menlo Park, CA (US)

( * ) Notice: Subject to any disclaimer, the term of this patent is extended or adjusted under 35 U.S.C. 154(b) by 608 days.

This patent is subject to a terminal disclaimer.

(21) Appl. No.: 13/343,407

(22) Filed: Jan. 4, 2012

(65) Prior Publication Data

US 2013/0172790 A1    Jul. 4, 2013

(51) Int. Cl.
*A61F 9/00* (2006.01)
*A61F 7/02* (2006.01)
(Continued)

(52) U.S. Cl.
CPC .................. *A61F 7/02* (2013.01); *A61F 9/00* (2013.01); *A61F 13/00063* (2013.01); *A61H 23/0245* (2013.01); *A61H 23/0263* (2013.01); *A61F 7/034* (2013.01); *A61F 7/106* (2013.01); *A61F 9/04* (2013.01); *A61F 2007/0004* (2013.01); *A61F 2007/0071* (2013.01); *A61F 2007/0096* (2013.01); *A61F 2007/0226* (2013.01); *A61F 2013/0028* (2013.01); *A61F 2013/00187* (2013.01); *A61F 2013/00497* (2013.01); *A61F 2013/00502* (2013.01); *A61F 2013/00646* (2013.01); *A61H 2201/0188* (2013.01); *A61H 2201/0207* (2013.01);
(Continued)

(58) Field of Classification Search
CPC ..... A61H 1/00; A61F 9/00; A61F 7/02; A61F 7/007; A61F 2007/0226; A61F 7/08
USPC ........ 301/15, 37, DIG. 1; 602/1, 14; 607/96, 607/99, 108, 109, 111, 141; 219/528, 219/529
See application file for complete search history.

(56) References Cited

U.S. PATENT DOCUMENTS 2,108,934 A  *  2/1938  Albright ........................ 607/104
3,075,527 A  *  1/1963  Bechtold ....................... 604/294
(Continued)

FOREIGN PATENT DOCUMENTS

CN          203564408       4/2014
CN          205234758       5/2016
(Continued)

*Primary Examiner* — Justine Yu
*Assistant Examiner* — Christopher Miller
(74) *Attorney, Agent, or Firm* — Levine Bagade Han LLP

(57) ABSTRACT

Dry eye treatment apparatus and methods are described herein which generally includes a patch or strip affixed to the skin of the upper and/or lower eyelids to deliver heat or other forms of energy, pressure, drugs, moisture, etc. (alone or in combination) to the one or more meibomian glands contained within the underlying skin. The treatment strip or strips include one or more strips configured to adhere to an underlying region of skin in proximity to one or both eyes of a subject such that the one or more strips allow for the subject to blink naturally without restriction from the one or more strips. Moreover, the one or more strips may be configured to emit energy to the underlying region of skin and where the one or more strips are shaped to follow a location of one or more meibomiam glands contained within the underlying region of skin.

66 Claims, 20 Drawing Sheets

(51) Int. Cl.
  *A61F 13/00* (2006.01)
  *A61H 23/02* (2006.01)
  *A61M 35/00* (2006.01)
  *A61F 9/04* (2006.01)
  *A61F 7/03* (2006.01)
  *A61F 7/10* (2006.01)
  *A61F 7/00* (2006.01)

(52) U.S. Cl.
  CPC ............... *A61H 2201/0214* (2013.01); *A61H 2201/0228* (2013.01); *A61H 2201/0257* (2013.01); *A61H 2201/0278* (2013.01); *A61H 2201/10* (2013.01); *A61H 2201/105* (2013.01); *A61H 2201/5002* (2013.01); *A61H 2201/5035* (2013.01); *A61H 2201/5038* (2013.01); *A61H 2201/5041* (2013.01); *A61H 2201/5082* (2013.01); *A61H 2205/024* (2013.01); *A61M 35/00* (2013.01)

(56) References Cited

U.S. PATENT DOCUMENTS

| | | | | |
|---|---|---|---|---|
| 3,173,419 | A * | 3/1965 | Dubilier et al. | 607/109 |
| 4,261,364 | A | 4/1981 | Haddad et al. | |
| 4,325,254 | A * | 4/1982 | Svacina et al. | 607/114 |
| 4,867,146 | A * | 9/1989 | Krupnick | A61F 9/00 128/858 |
| 4,930,317 | A * | 6/1990 | Klein | 62/3.3 |
| 4,962,761 | A * | 10/1990 | Golden | 607/104 |
| 5,097,829 | A * | 3/1992 | Quisenberry | A61F 7/02 219/490 |
| 5,164,987 | A | 11/1992 | Raven | |
| 5,643,336 | A * | 7/1997 | Lopez-Claros | 607/104 |
| 6,066,164 | A * | 5/2000 | Macher et al. | 607/96 |
| 6,074,414 | A * | 6/2000 | Haas et al. | 607/108 |
| 6,155,995 | A * | 12/2000 | Lin | 601/15 |
| D441,081 | S | 4/2001 | Mueller | |
| 6,238,427 | B1 * | 5/2001 | Matta | 607/104 |
| 6,416,534 | B1 * | 7/2002 | Montagnino et al. | 607/114 |
| 6,511,446 | B1 * | 1/2003 | Wu | 601/15 |
| 6,860,880 | B2 | 3/2005 | Treat et al. | |
| 6,908,195 | B2 | 6/2005 | Fuller, Jr. | |
| D507,054 | S | 7/2005 | Mueller et al. | |
| D507,055 | S | 7/2005 | Mueller et al. | |
| D507,350 | S | 7/2005 | Mueller et al. | |
| D507,651 | S | 7/2005 | Mueller et al. | |
| 6,923,988 | B2 | 8/2005 | Patel et al. | |
| D511,573 | S | 11/2005 | Mueller et al. | |
| D513,323 | S | 12/2005 | Mueller et al. | |
| 7,108,694 | B2 | 9/2006 | Miura et al. | |
| 7,211,070 | B2 | 5/2007 | Soroudi | |
| D613,408 | S | 4/2010 | Gausmann et al. | |
| D614,303 | S | 4/2010 | Gausmann et al. | |
| D614,774 | S | 4/2010 | Gausmann et al. | |
| D617,443 | S | 6/2010 | Grenon et al. | |
| 7,758,190 | B2 | 7/2010 | Korb et al. | |
| 7,833,205 | B2 | 11/2010 | Grenon et al. | |
| D638,128 | S | 5/2011 | Prokop et al. | |
| 7,976,573 | B2 | 7/2011 | Korb et al. | |
| 7,981,095 | B2 | 7/2011 | Grenon et al. | |
| 7,981,145 | B2 | 7/2011 | Korb et al. | |
| 7,981,146 | B2 | 7/2011 | Korb et al. | |
| 7,981,147 | B2 | 7/2011 | Korb et al. | |
| 7,988,294 | B2 | 8/2011 | Korb et al. | |
| 8,007,524 | B2 | 8/2011 | Korb et al. | |
| 8,025,689 | B2 | 9/2011 | Korb et al. | |
| 8,506,539 | B2 | 8/2013 | Guillon et al. | |
| 8,535,363 | B1 * | 9/2013 | Lewis | 607/109 |
| 9,510,972 | B2 | 12/2016 | Badawi | |
| 2002/0117495 | A1 * | 8/2002 | Kochman | H05B 3/34 219/549 |
| 2003/0167556 | A1 | 9/2003 | Kelley | |
| 2004/0116990 | A1 * | 6/2004 | Agarwal et al. | 607/114 |
| 2005/0119629 | A1 * | 6/2005 | Soroudi | 604/289 |
| 2005/0187502 | A1 * | 8/2005 | Krempel et al. | 602/5 |
| 2006/0018953 | A1 | 1/2006 | Guillon et al. | |
| 2006/0069420 | A1 * | 3/2006 | Rademacher et al. | 607/141 |
| 2006/0154642 | A1 | 7/2006 | Scannell | |
| 2006/0200052 | A1 * | 9/2006 | Lin | 601/70 |
| 2006/0235497 | A1 * | 10/2006 | Zanotti | 607/104 |
| 2007/0016255 | A1 * | 1/2007 | Korb et al. | 607/1 |
| 2007/0060988 | A1 | 3/2007 | Grenon et al. | |
| 2008/0039749 | A1 * | 2/2008 | Kopanic et al. | 601/46 |
| 2008/0081999 | A1 * | 4/2008 | Gravely et al. | 600/473 |
| 2008/0109053 | A1 * | 5/2008 | Grenon et al. | 607/109 |
| 2008/0114421 | A1 | 5/2008 | Korb et al. | |
| 2008/0114423 | A1 * | 5/2008 | Grenon et al. | 607/96 |
| 2008/0114424 | A1 | 5/2008 | Grenon et al. | |
| 2008/0132978 | A1 * | 6/2008 | Korb et al. | 607/109 |
| 2009/0020521 | A1 * | 1/2009 | Blaszczykiewicz et al. | 219/529 |
| 2009/0048590 | A1 | 2/2009 | Conrad et al. | |
| 2009/0137533 | A1 | 5/2009 | Adkins, Jr. | |
| 2009/0149925 | A1 | 6/2009 | MacDonald et al. | |
| 2009/0312823 | A1 * | 12/2009 | Patience et al. | 607/104 |
| 2010/0010598 | A1 | 1/2010 | Igaki et al. | |
| 2010/0114086 | A1 * | 5/2010 | Deem et al. | 606/33 |
| 2010/0174501 | A1 | 7/2010 | Myadam | |
| 2010/0267751 | A1 | 10/2010 | Beals et al. | |
| 2011/0046581 | A1 | 2/2011 | Linder | |
| 2011/0081333 | A1 * | 4/2011 | Shantha et al. | 424/94.62 |
| 2011/0275410 | A1 | 11/2011 | Caffey et al. | |
| 2012/0062840 | A1 | 3/2012 | Ballou et al. | |
| 2012/0191164 | A1 | 7/2012 | Gander et al. | |
| 2012/0213840 | A1 | 8/2012 | Lim | |
| 2013/0046367 | A1 | 2/2013 | Chen | |
| 2013/0172829 | A1 | 7/2013 | Badawi | |
| 2013/0281893 | A1 * | 10/2013 | Yang | 601/15 |
| 2016/0106576 | A1 | 4/2016 | Badawi et al. | |
| 2017/0079834 | A1 | 3/2017 | Badawi | |
| 2017/0079840 | A1 | 3/2017 | Badawi | |

FOREIGN PATENT DOCUMENTS

| | | |
|---|---|---|
| DE | 29920352 | 3/2000 |
| JP | 2003-093431 | 4/2003 |
| JP | 2007-185017 | 7/2007 |
| JP | 2011-188958 | 9/2011 |
| WO | WO 99/20213 | 4/1999 |
| WO | WO 00/69506 | 11/2000 |
| WO | WO 02/067688 | 9/2002 |
| WO | WO 02067688 A1 * | 9/2002 |
| WO | WO 2004006801 A2 * | 1/2004 |
| WO | WO 2004/006801 | 11/2004 |
| WO | WO 2006/099413 | 9/2006 |
| WO | WO 2008/085162 | 7/2008 |
| WO | WO 2008085162 A1 * | 7/2008 |
| WO | WO 2008/100647 | 8/2008 |
| WO | WO 2008100647 A1 * | 8/2008 |
| WO | WO 2013/103413 | 7/2013 |

* cited by examiner

DRY EYE TREATMENT APPARATUS AND METHODS

FIELD OF THE INVENTION

The present invention relates to methods and apparatus for treatment of dry eye syndrome and other related conditions. More particularly, the present invention relates to methods and apparatus for the treatment of dry eye syndrome using adhesive strips which are specifically contoured or shaped to adhere to selected regions around a patient's eyes or peri-orbital region.

BACKGROUND OF THE INVENTION

Tears are a complex mixture of water, lipids, mucus, proteins and electrolytes and this mixture helps to maintain a smooth and clear optical surface and also helps to protect the eyes from infection. The tear film has three basic layers: oil, water, and mucus and problems or disturbances in any of these layers can cause dry eyes symptoms.

The outermost layer of the tear film is typically comprised of an oil layer containing fatty acids and lipids (meibum) which are produced primarily by sebaceous glands called the meibomian glands located along the eyelid margin. The oil layer smoothes the tear surface and slows evaporation of the watery middle layer. However, if the meibomian glands fail to produce enough oil, produce suboptimal fatty acid mixtures, or if the glands become obstructed or clogged, the watery layer typically evaporates too quickly causing dry eyes. A blockage of the meibomian glands can lead to enlarged glands or infections. Dry eyes are thus common in people whose meibomian glands are obstructed or functioning improperly.

The middle layer of tears is composed primarily of an aqueous solution, which is produced by the lacrimal glands (tear glands). The middle layer cleanses the eyes and washes away foreign particles or irritants, maintains a clear optical medium, and keeps the ocular surface moist. The innermost layer of the tear film is composed primarily of mucus which helps to spread the tears evenly over the surface of the eyes. A lack of mucus in the tear film is also associated with dry eye syndrome.

As discussed above, the meibomian glands are oil-secreting glands located within both the upper and lower eyelids. There are approximately 30 to 40 glands along the upper eyelid and approximately 20 to 30 glands along the lower eyelid with the ducts for each of the glands opening along the inner edge of the free margin of the respective lids by minute foramina through which their secretion is released to prevent the lids adhering to each other. An example of the location of the meibomian glands is illustrated in the cross-sectional view of the upper eyelid UL shown in FIG. 1A which illustrates the relative positioning of a single meibomian gland MG. Other glands and anatomical features are illustrated for reference, e.g., the glands of Wolfring GW, tarsus TR, gland of Moll GM, gland of Zeis GZ, gland of Krause GK, upper formix UF, conjunctiva CN and cornea CR of the eye which is partially covered by the upper eyelid UL. As illustrated, the meibomian gland MG is positioned along a length of the upper eyelid UL (and lower eyelid LL) with the duct opening along the inner edge of the eyelid UL in proximity to a surface of the underlying eye.

FIG. 1B illustrates a front view of a patient's eye having the upper eyelid UL and lower eyelid LL in a closed position, such as when the patient blinks. As shown, the meibomian glands MG may be seen aligned adjacent to one another over both the upper UL and lower eyelids LL. FIG. 1C also shows a perspective view of a patient's eye in the open position to illustrate how the meibomian glands are typically aligned relative to one another when the patient's eye is opened.

Blinking is thought to be the primary mechanism to open the orifice of the meibomian glands to allow for the release of oil secretions from the glands. The natural blinking motion and blinking force causes the upper lid to pull a sheet of the lipids secreted by the meibomian glands over the two underlying layers of the tear film thus forming the protective coating which limits the rate at which the underlying layers evaporate. It is estimated that approximately 65% of meibomian gland disease or dry eye results from a defective lipid layer or an insufficient quantity of such lipids that results in accelerated evaporation of the aqueous layer. Hence, blinking disorders, or other disorders that affect proper tear distribution, may also cause or exacerbate meibomian gland dysfunction or dry eye.

As the eyelids close in a total blink, the superior and inferior formices, which hold a reservoir of tears, are compressed by the force of the preseptal muscles and the eyelids move toward one another. The upper eyelid, for instance, moves over the eye while exerting upon the eye surface a force which helps to clear the front of the eye of debris, insoluble mucin, and also expresses the oil secretions from the meibomian glands. The lower lid moves horizontally in the nasal direction and pushes debris toward both punctae, the openings that ultimately drain into the nasal cavities.

As the eyelids open the tear film is redistributed where the upper lid pulls the aqueous phase via capillary action and the lipid layer spreads as quickly as the eyelids move. Hence, eyelid movement is accordingly important in tear-film renewal, distribution, turnover, and drainage.

For a variety of reasons, the meibomian glands can become blocked, plugged, or occluded resulting in meibomian gland dysfunction and dry eye disease. The obstruction that triggers the disease can occur anywhere within the meibomian gland, for instance, at the gland's surface or orifice preventing normal lipid secretions from flowing; in the main channel of the gland which may be narrowed or blocked; or in other locations deeper within the gland that lead to the main channel.

Treatments for blocked meibomian glands may include a number of conventional treatments. One course of treatment includes the application of soap and cleaning agents, eyelid scrubs, or antibiotics to reduce eyelid inflammation. Antibiotics such as tetracycline, doxycycline, metronidazole, or erythromycin can be administered orally or topically to help regulate or improve meibomian gland lipid production. Inflammation on the surface of the eye may also be controlled with topical drugs such as corticosteroids or cyclosporine (RESTASIS®, Allergan, Inc., CA), or other anti-inflammatory compounds or immune-suppressants. Evidence suggests that ocular surface inflammation is not only associated with meibomian gland dysfunction but also with dry eye syndrome.

Other examples of dry eye treatments may include the application of prescription eye inserts for people with moderate to severe dry eyes symptoms who are unable to use artificial tears. An eye insert, e.g., hydroxypropyl cellulose (LACRISERT®, Merck & Co., Inc., NJ), may be inserted between the lower eyelid and eye. The insert dissolves slowly to release a substance which lubricates the eye. Alternatively, special contact lenses may be used to shield the surface of the eye to trap moisture.

In other treatments, the patient's tear ducts may be closed to prevent the tear film from draining away from the surface of the eye too quickly by procedures such as insertion of punctal plugs into the tear ducts or cauterizing the tissues of the drainage area. Aside from implants or cauterizing treatments, dry eye syndrome may be treated using pharmaceutical agents such as eyedrops, ointments which coat the eyes, etc. Artificial tears, gels, ointments, autologous serum tears, or albumin drops have all been employed in the treatment of dry eye.

Additionally, warm compresses are also typically placed over the eyes and are used to restore function to the meibomian glands by melting any lipid plugs as well as incorporating massaging of the lids which may further express meibomian gland contents. However, application of warm compresses require their application two to three times daily during which time patients may incorrectly target only one of the affected lids and are also prevented from seeing out of the treated eye because of the compresses. Compresses may be too hot, further exacerbating inflammation, or they may cool too quickly preventing adequate therapeutic effect.

Other treatment devices have also been developed which cover the entire affected eye to apply heat and a massaging force directly to the affected eyelids. However, such devices, like the compresses, require that the patient's eyes be temporarily but completely obstructed during the treatment resulting in discomfort, lost productivity, and potentially lower compliance among patients. Additionally, these treatments require visits to a physician or healthcare provider and are not as well-suited for widespread consumer adoption.

Accordingly, there exists a need for methods and apparatus which are relatively simple to routinely use for the patient, which also allow for the patient to continue their normal activities, is non-obtrusive and non-disruptive, and which also take advantage of the patient's natural physiological activities to facilitate treatment.

SUMMARY OF THE INVENTION

In treating conditions such as meibomian gland dysfunction or dry eye syndrome, a patch or strip can be affixed to the skin of the upper and/or lower eyelids to deliver heat or other forms of energy, pressure, drugs, moisture, etc. (alone or in combination) to the one or more meibomian glands contained within the underlying skin. In particular, the assembly for the treatment strip or strips may generally comprise one or more strips configured to adhere to an underlying region of skin in proximity to one or both eyes of a subject such that the one or more strips allow for the subject to blink naturally without restriction from the one or more patches. Moreover, the one or more strips may be configured to emit energy to the underlying region of skin and where the one or more strips are shaped to follow a location of one or more meibomian glands contained within the underlying region of skin.

In use, the one or more strips may be adhered to a region of skin in proximity to one or both eyes of a subject such that the one or more strips allow for the subject to blink naturally without restriction from the one or more patches. While adhered, the strips may emit energy to the region of skin, where the one or more strips are shaped to follow a location of one or more meibomian glands contained within the region of skin. Alternatively, while the strip may not directly overly a meibomian or other ocular or orbital gland, it may deliver energy or absorb energy from underlying neighboring vasculature which ultimately supplies said glands. In other words, heating or cooling the blood supply to the eyelids, meibomian glands, and/or lacrimal glands using these strips may affect their function and metabolism while not necessarily needing to directly overly them in particular variations.

The upper strip may thus have an upper curved or arcuate periphery which is shaped to extend and follow the upper (or superior) border of the meibomian glands (such as along or up to the upper eyelid crease) while the straightened periphery of the lower edge may be shaped to extend and follow the lower (or inferior) border of the meibomian glands such as along the free margin of the upper eyelid. Although straightened, the lower edge may be gently curved or arcuate in alternative variations. The lower strip may similarly have an upper straightened periphery to extend and follow the upper (or superior) border of the meibomian glands along the free margin of the lower eyelid and a lower curved or arcuate periphery to extend and follow the lower (or inferior) border of the meibomian glands along the lower eyelid (such as along or up to the lower eyelid crease). Alternatively, the upper periphery of the lower strip may also be gently curved or arcuate in alternative variations as well.

In other words, with the tarsal plate containing the meibomian glands which span from proximal to distal, the peripheral edges of the treatment strips may correspond to the distal eyelid margin and proximal peripheral edge and the treatment strips can assume multiple configurations. Generally, the peripheral distal edge of the treatment strip may be relatively straight or assume a gentle curve either of which can follow the underlying distal eyelid margin and tarsal plate while having a proximal peripheral edge that is relatively curved to assume the more curved proximal edge of the underlying tarsal plate.

The strips may be used individually for placement upon only the upper eyelid or only the lower eyelid depending upon the desired treatment. Moreover, the lengths of the treatment strips may also be varied to target individual meibomian glands for providing a targeted treatment, if desired, and as described in further detail herein. Additionally, while the treatment strips may be sized generally, they may also be custom made or sized for a specific individual's eyelid dimensions.

Because of the specific contoured sizes and flexibility of the treatment strips the treatment strips may be placed upon the patient to apply therapy to the underlying meibomian glands allowing the patient's eyes to be opened and closed normally without interference from one or both treatment strips. Accordingly, the treatment strips contoured size, shape, and flexibility allow for treatment to occur while also allowing for the patient to have one or both eyes remain opened such that normal, physiologic blinking can proceed during the course of treatment. Rather than relying on an application of any type of external force, the treatment strips take advantage of the eye's natural mechanism for clearing oil from the meibomian glands via blinking. Hence, the treatment strips may be adhered in place for treatment without any further intervention by the patient or healthcare provider such that the treatment strips may apply, e.g., heat energy, to melt or liquefy any waxy or solid meibomian gland obstructions while the eyes remain unobstructed and are allowed to blink naturally. The treatment strips thus allow for the natural blinking force to clear the glands of the heat-treated softened obstructions before they have re-solidified unlike other treatments which require that the patient keep their eyes closed or obstructed during the course of a treatment and prevent or inhibit the patient from blinking.

The treatment strip may be configured to have a contact layer (e.g., fabricated from conductive materials such as metals, alloys, porous ceramics, engineering ceramics, woods, polymers, composites, foams, polymer foams, fabrics, elastomers, etc.) which may protect the skin from burns or any other adverse effects. A second heating layer may be positioned above the contact layer (or directly in contact against the skin) for generating the heat energy and an insulative layer may be positioned atop the heating layer for focusing, directing, or reflecting the heat towards the underlying skin surface as well as to protect the patient from contact with the heating layer from other parts of the body. The insulative layer may accordingly be fabricated from a variety of insulative materials, e.g., foams, foam tapes, gauze, silicone, microporous polyethylene films, fabrics, polymers, etc.

Although the application of heat energy from the treatment strips is described, other variations may alternatively include the application of using the treatment strips for cooling of the underlying skin. Rather than using the heating layer in an exothermic reaction, the layer may be configured to utilize an endothermic reaction instead to provide for cooling of the skin Cooling, rather than heating, may be applied for conditions such as reducing inflammation, alleviating allergies or tired eyes, etc. particularly as the patient rests or sleeps.

Aside from the application of heat energy from the treatment strips, the strips may also include a layer for the diffusion or release of one or more pharmaceutical, biological, or chemical agents either alone or in combination with the heat treatment. For instance, the pharmaceutical, biological, or chemical agents may be incorporated into the either the contact layer, insulative layer, or in a separate layer entirely, for transdermal delivery to the meibomian glands or to the areas surrounding the meibomian glands for additional and/or alternative treatments. In the event that the pharmacological or chemical agent is released during the heat treatment, the heat may help to improve penetration of any drugs into the underlying skin.

While the treatment strips may incorporate various layers into the strips to effect various different treatments, the strips may also be varied in size, shape, contour, etc. depending upon the desired treatment areas so long as the treatment strips are contoured or shaped to follow the location of at least one meibomian gland.

While the treatment strips may be applied to one or more of the meibomian glands, variations of the strip may also be used to treat other glands such as the sebaceous glands, e.g., for acne treatment. Treatment strips used to treat acne may utilize different pharmacological treatments. Moreover, the treatment strips may be used to potentially treat eye disorders beyond meibomian gland dysfunction.

Yet another example may include use of the treatment strips for treating disorders of the lacrimal gland and/or palpebral lacrimal gland which are located above the eye. Variously sized treatment strips, such as lacrimal gland strips which are sized to have a curved upper periphery, may be sized for placement directly over the skin surface above where the lacrimal glands are located. The lacrimal glands and/or palpebral lacrimal gland may be treated alone or in combination with the treatment strips contoured for treatment of the meibomian glands.

While the treatment strips may be applied over the meibomian glands to apply the heat energy, the treatment does not require the application of any external force applied by the strip or any other external device but may utilize the natural blinking of the patient to facilitate treatment. However, in additional variations, the treatment strips may be configured to apply both the heat treatment as well as an external force. Any number of mechanisms may be utilized to apply a pinching or biasing force to provide for compression of the underlying skin and of the meibomian glands during application of the heat therapy.

Aside from a compression force, the strip may be formed with alternative components such as a mechanical component to impart vibrational energy or other forms of energy to facilitate the expression of the meibomian glands and promote oil secretion.

In yet another variation, one or both treatment strips may be configured to incorporate an indicator, e.g., LED light, alarm, vibration element, etc., electrically coupled to a power supply and/or processor to alert the patient when a prescribed treatment has been completed. This feature (and any of the other features) may be combined with any of the other variations of the treatment strips described herein as practicable.

With the incorporation of a processor into the treatment strips, treatment times or other parameters such as temperature of the strips may be programmed and optionally shut on or off selectively by the patient or automatically. Moreover, other parameters such as the frequency of the heat delivery or other stimulation may also be programmed by the processor to provide further flexibility in treatment.

DETAILED DESCRIPTION OF THE INVENTION

In treating conditions such as meibomian gland dysfunction (MGD), which is commonly associated with the evaporative form of dry eye syndrome (DES), a patch, strip or thin adhesive device can be affixed to the skin of the upper and/or lower eyelids to deliver heat or other forms of energy, pressure, drugs, moisture, etc. (alone or in combination) to the one or more meibomian glands contained within the underlying skin. In particular, the treatment strip or strips may be configured and sized specifically for placement over one or more targeted meibomian glands contained within the skin of the upper and/or lower eyelids. The application of thermal therapy, e.g., heating or cooling, can cross the eyelids quite easily as the eyelids are generally the thinnest skin found on the human body and the tissue is highly vascularized. With the root of the eyelid located proximally and the eyelid margin located distally, the net arterial flow of blood flows from proximal to distal. So wherever these treatment strips are placed, the heating or cooling therapy may easily be carried throughout the eyelid and any structures contained therein, e.g., meibomian glands MG, lacrimal glands LG, gland of Zeis GZ, gland of Moll GM, gland of Wolfring GW, gland of Kraus GK, etc.

Moreover, because the eyelid is so thin, the heating or cooling therapy can be transmitted to the ocular surface and the eye itself (described in further detail below). Thus, the therapy can impart energy to the conjunctiva, goblet cells, episcleral vasculature, cornea, aqueous humor, iris, ciliary body, and possibly the anterior vitreous and lens. Thus, any thermal therapy by the treatment strips may also impact and be used to treat ocular surface disorders and anterior segment diseases, e.g., conjunctivitis, keratitis, keratopathy, iritis, cyclitis, glaucoma, cataract, etc. Also, there may be use in the postoperative state-like after LASIK, PRK, or cataract or corneal surgery or other ocular, peri-ocular, intraocular, or eyelid surgery, as described in further detail below.

Figure 1A:
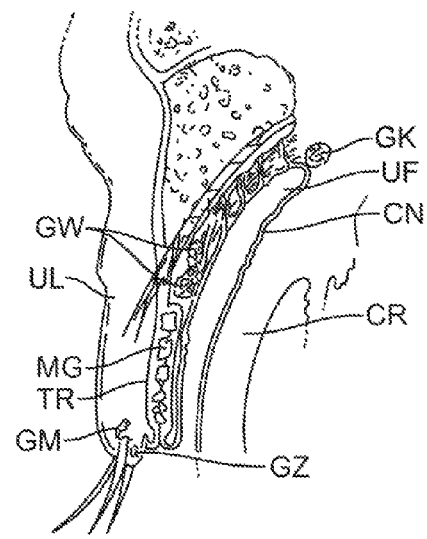
FIG. 1A shows a cross-sectional side view of an upper eyelid and an example of the location of a meibomian gland.
Figure 1B:
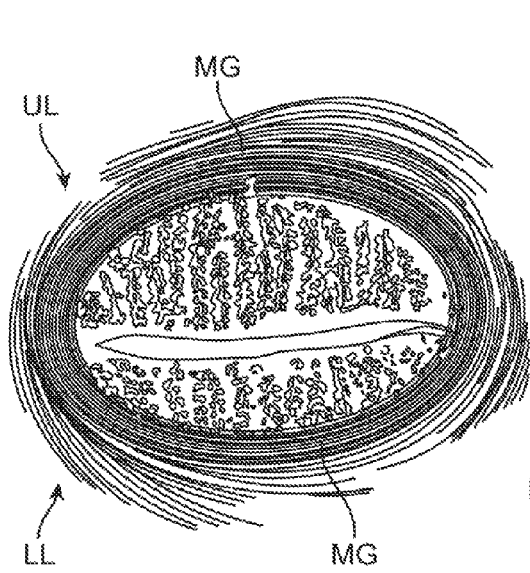
FIG. 1B shows a front view diagram of meibomian gland distribution in human eyelids having the upper eyelid and lower eyelid in a closed position, such as when the patient blinks, and the alignment of the meibomian glands over both the upper and lower eyelids.
Figure 1C:
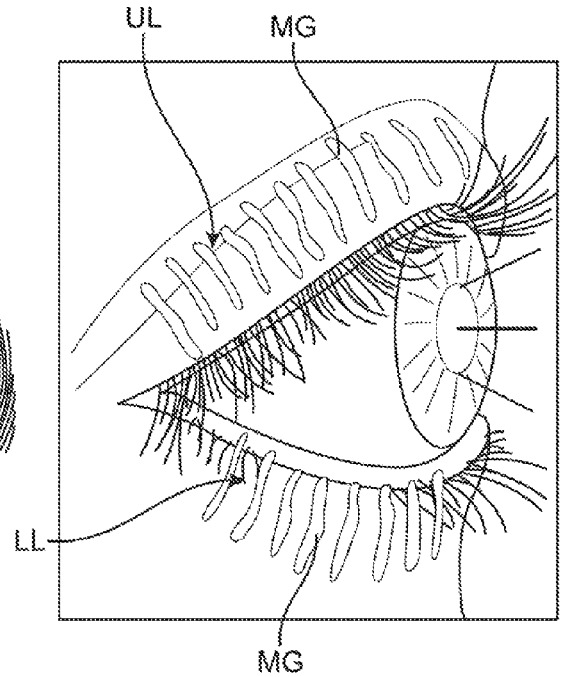
FIG. 1C shows a perspective view of a patient's eye in the open position to illustrate how the meibomian glands are typically aligned relative to one another when the patient's eye is opened.
Figure 2A:
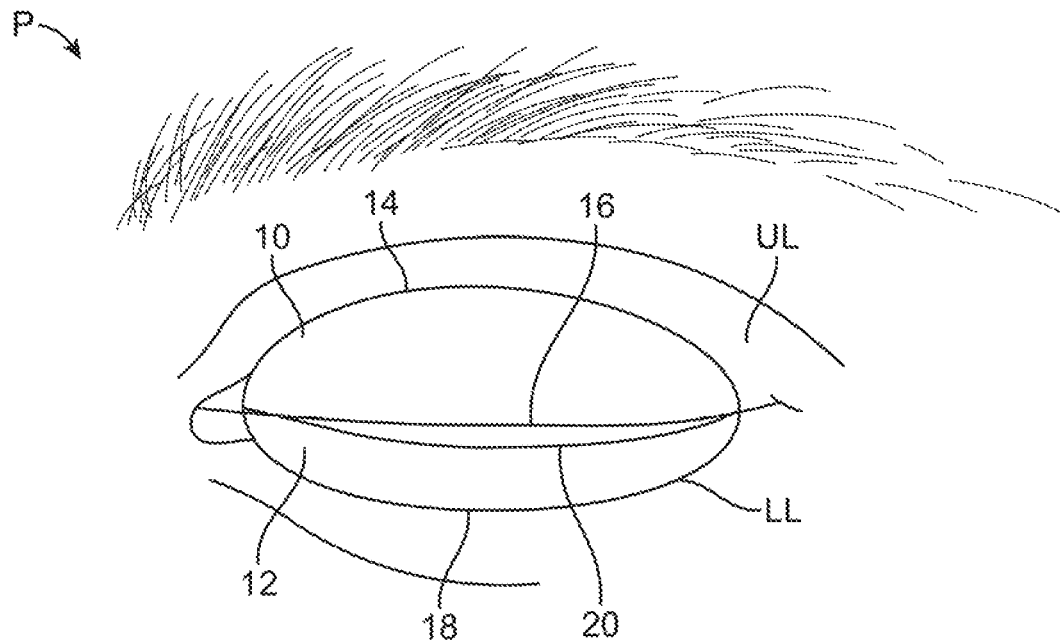
FIG. 2A shows a front view of a patient's eye in a closed position with an example of treatment strips which adhere onto the upper or lower eyelids (or both) and where the strips are sized or contoured for placement directly over the meibomian glands located in the underlying eyelids.
Figure 2B:
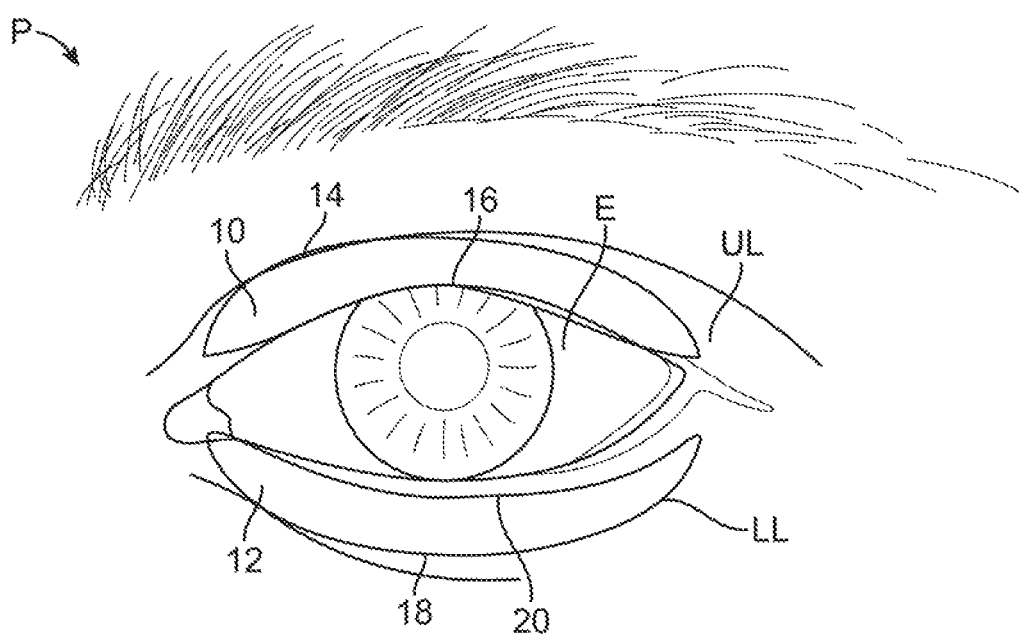
FIG. 2B shows the treatment strips of FIG. 2A illustrating how the strips may remain adhered to the patient skin while allowing for the eyelids to retract and allow for the patient to continue blinking while viewing normally out of the eye. While the strips may be applied from eyelid margin to eyelid crease, they may alternatively flex or accordion and/or compress during blinks to prevent impairment of normal blinking and maximize comfort.

As shown in the front view of FIG. 2A and FIG. 2B, one variation of such treatment strips may be seen as being adhered temporarily upon the upper eyelid UL and lower eyelid LL over an eye E of a patient P when closed for illustrative purposes. The contoured upper strip 10 may be sized for adherence directly upon the skin of the upper eyelid UL such that the strip 10 has a configuration and shape which follows the location of the one or more meibomian glands contained within the underlying skin of the upper eyelid UL. Likewise, the contoured lower strip 12 may also have a configuration and shape which follows the location of the one or more meibomian glands contained within the underlying skin of the lower eyelid LL. In other variations, the contoured strip may stop at the eyelid crease or cross over it as described in other variations below.

The upper strip 10 may thus have an upper curved or arcuate periphery 14 which is shaped to extend and follow the upper (or superior) border of the meibomian glands (such as along or up to the upper eyelid crease) while the straightened periphery 16 of the lower edge may be shaped to extend and follow the lower (or inferior) border of the meibomian glands such as along the free margin of the upper eyelid UL. The lower strip 12 may similarly have an upper straightened periphery 20 to extend and follow the upper (or superior) border of the meibomian glands along the free margin of the lower eyelid LL and a lower curved or arcuate periphery 18 to extend and follow the lower (or inferior) border of the meibomian glands along the lower eyelid LL (such as along or up to the lower eyelid crease). The use of the terms lower and upper herein refer to the periphery of the treatment strips when placed upon the patient P (human or animal) and are used herein for descriptive purposes.

While the treatment strips 10, 12 are both shown adhered upon the respective upper eyelid UL and lower eyelid LL, the strips 10, 12 may be used individually for placement upon only the upper eyelid UL or only the lower eyelid LL depending upon the desired treatment. Moreover, the lengths of the treatment strips 10, 12 may also be varied to target individual meibomian glands for providing a targeted treatment, if desired, and as described in further detail herein.

While the treatment strips 10, 12 are shown placed upon the closed eyelids of the patient P, the strips 10, 12 are arc-shaped or flexible enough to assume the curvature of the patient's eyelid margin and may be long enough to cover some or all of the underlying meibomian glands in the tarsal plate. While the treatment strips 10, 12 may be sized generally, they may also be custom made or sized for a specific individual's eyelid dimensions or shaped to optimize adhesion and/or comfort and/or stability. Generally, the treatment strips 10, 12 may have a length anywhere from about 1 mm to 50 mm depending upon the desired treatment length as well as the anatomical considerations of the patient since the typical palpebral fissure length in an adult is about 27 mm to 30 mm. Thus, to cover as many as all of the meibomian glands, the treatment strips 10, 12 may be sized to have length of, e.g., 25 mm to 30 mm, or if sized to cover just beyond all the meibomian glands, a length of, e.g., 30 mm to 50 mm (or more if needed to optimize adhesion/comfort/stability). Moreover, one or both treatment strips 10, 12 can have a width ranging anywhere from about 1 mm to 25 mm since the typical eyelid crease in a Caucasian male is about 8 mm to 9 mm above the eyelid margin while in Caucasian females it is about 9 mm to 11 mm above the eyelid margin (or more if needed for adhesion/comfort and potentially increased efficacy from heating or cooling the inbound blood flow). Customization enables it to fit any particular anatomy, race, ethnicity, etc. Moreover, the treatment strips may be manufactured with varying levels of flexibility to accommodate the ergonomics of the eyelid and eyelid blink for optimal comfort and minimal obtrusiveness or movement.

Because of the specific contoured sizes and flexibility of the treatment strips 10, 12, the treatment strips may be placed upon the patient P by the patient himself/herself for consumer use or by a healthcare provider to apply therapy to the underlying meibomian glands allowing the patient's eyes to be opened and closed normally, as shown in FIG. 2B, without interference from one or both treatment strips. While the strips may be applied from eyelid margin to eyelid crease, they may alternatively flex or accordion and/or compress during blinks to prevent impairment of normal blinking and maximize comfort.

Typical treatment patches, such as for application of a warm compress, are generally sized for placement over the entire eye or eyes such that the patient is unable to open their eyes or blink during a treatment session. Yet, because of the strong association between DES and MGD (for instance, MGD includes the spectrum of MGD, meibomitis, blepharitis, and ocular rosacea), natural blinking by an individual is the mechanism by which meibomian gland secretions are normally released onto the eyelid margin and over the tear. In the absence of blinking, the oil contained within the meibomian glands remain unexpressed within the glands' terminal ducts and fail to contribute to distribution of the oily layer upon the tears.

Accordingly, the treatment strips 10, 12 contoured size, shape, and flexibility allow for treatment to occur while also allowing for the patient to have one or both eyes remain opened such that normal, physiologic blinking can proceed during the course of treatment. Rather than relying on an application of any type of external force to express the oil or obstruction from the glands, the treatment strips 10, 12 take advantage of the eye's natural mechanism for clearing oil from the meibomian glands via blinking. Hence, the treatment strips 10, 12 may be adhered in place for treatment without any further intervention by the patient or healthcare provider such that the treatment strips 10, 12 may apply, e.g., heat energy, to melt or liquefy any waxy or solid meibomian gland obstructions while the eyes remain unobstructed and are allowed to blink naturally. The treatment strips 10, 12 thus allow for the natural blinking to clear the glands of the heat-treated softened obstructions before they have re-solidified unlike other treatments which require that the patient keep their eyes closed or obstructed during the course of a treatment and prevent or inhibit the patient from blinking Delivery of heat may also increase blood flow by promoting vasodilation as increased delivery of blood can affect metabolism, temperature of other tissues, may have effects on inflammation, and can thereby improve tissue function.

Because some patients have obstructions or occlusions in their meibomian glands that may not sufficiently melt, loosen, or soften without attaining heightened temperatures at the meibomian glands, the treatment strips 10, 12 may apply heat or other treatments to the surface of the eyelids for a significant period of time for relatively longer treatment times and at higher treatment temperatures because of the ability of the treatment strips 10, 12 to remain attached to the patient during any given period throughout the day. Patients can assume their daily activities with their eyes open and eyes blinking and with the comfort of a strip-based treatment. Moreover, patients can affix the treatment strips as many times as needed throughout the day, week, month, etc. until dry eye symptoms subside. This increases the frequency of treatment, convenience of treatment, and thus efficacy of treatment.

Because of the prolonged treatment times, the application of a separate force beyond the application of the strips may not be needed so long as the patient is able to continue blinking during the course of treatment. Moreover, the treatment frequency may be varied depending upon the severity of the condition to be treated. One example for potential treatment frequency may include application of one or both strips, e.g., up to six times per day for ten minutes or up to an hour or more for each treatment. Moreover, because the treatment strips are positioned over the meibomian glands which overlie the ocular surfaces, the application of the heating therapy may also indirectly heat the ocular surface as well and may further reduce any chronic ocular surface inflammation, chronic conjunctival inflammation, or corneal neovascularization.

Aside from heating of the ocular surface, heat therapy may also optionally be used to potentially provide for indirect heating through the ocular surface as well for heating of the retina to provide a thermal therapy to limit inflammation and neovascularization which are underlying conditions for diseases such as Wet age-related macular degeneration (AMD) and Diabetic Retinopathy.

While the treatment strips 10, 12 may be used throughout the day to take advantage of the patient's physiologic blinking, the treatment strips 10, 12 may also be used while the patient is resting or sleeping or while the patient simply maintains their eyes closed.

Figure 3A:
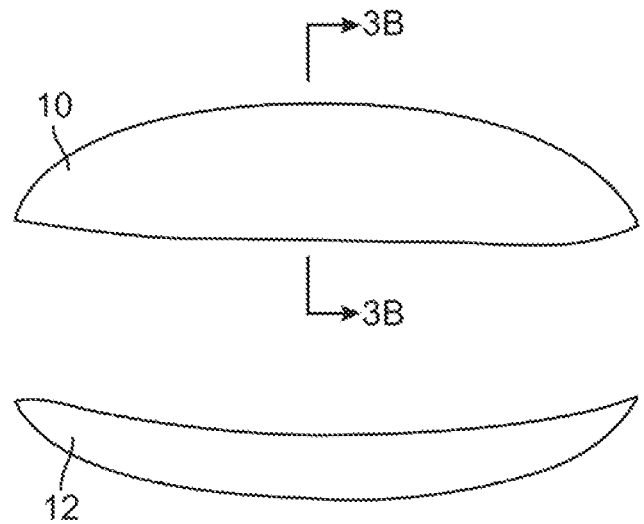
FIG. 3A shows an example of a contoured treatment strips.
Figure 3B:
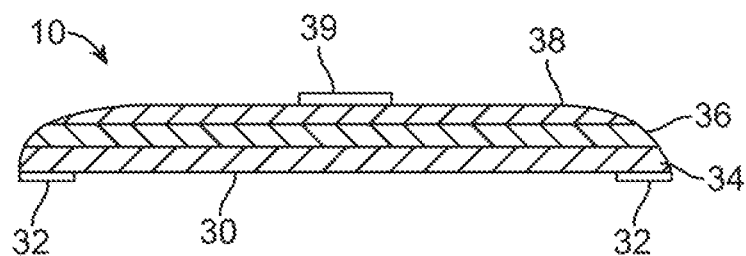
FIG. 3B shows an example of a cross-sectional side view of a treatment strip.

The treatment strips 10, 12 are desirably flexible enough to accommodate movement of the upper eyelid UL and/or lower eyelid LL which may move as much as about 15 mm or more. Thus, the treatment strips 10, 12 may be fabricated from various materials. FIGS. 3A and 3B show front and cross-sectional side views, respectively, in one example of a treatment strip configured to have an adhesive 32 positioned about a periphery of the strip to leave a contact region 30 for direct placement against the skin surface. The contact region 30 may further include a moisturizing layer to interface between the strip and skin to facilitate heat transfer from the strip as well as to provide moisturizing therapy to the skin. Alternatively, the treatment strips may be used with any number of moisturizing agents which may be applied to the underlying skin by the patient P or by a practitioner separately from the treatment strips. Moreover, the contact region 30 may be formed to have a surface which is smooth, porous, irregular, corrugated, etc. to facilitate contact and transfer of the heat from the treatment strip to the skin surface. Alternatively, the entire contact region 30, including its periphery, may be adhesive to maintain good contact. It may be hinged or curved to allow flexing or accordion-like dynamic movement for comfort and better, physiologically-sound ergonomics. In use, the strip may be applied under tension, as shown by the tensioned strip 10' in FIG. 3D, to further reduce any impairment to blinking and once adhered to the skin the strip may be released to allow for its flexion, as shown by the released strip 10" also in FIG. 3D, to facilitate blinking by the patient P.

In this variation, the treatment strip 10 may be configured to have a contact layer 34 (e.g., fabricated from conductive materials such as metals, alloys, porous ceramics, engineering ceramics, woods polymers, composites, foams, polymer foams, elastomers, etc.) which may protect the skin from burns or any other adverse effects. A second heating layer 36 may be positioned above the contact layer 34 (or directly in contact against the skin) for generating the heat energy and an insulative layer 38 may be positioned atop the heating layer 36 for focusing, directing, or reflecting the heat towards the underlying skin surface as well as to protect, the patient from contact with the heating layer 36 from other pans of the body. The insulative layer 38 may accordingly be fabricated from a variety of insulative materials, e.g., foams, foam tapes, gauze, silicone, microporous polyethylene films, metals, alloys, reflective materials, mirrors, etc. Moreover, the thickness of the treatment strip 10 may vary, e.g., anywhere from about 1/64" to 1/8" (about 0.397 mm to 3.175 mm) or more, depending upon the heating layer 36 mechanism as well as the desired thermal profile and targeted transmission temperature. Additionally and/or alternatively, the insulative layer 38 may be comprised of a thermochromic material which may change its color when a targeted temperature has been reached by the treatment strip 10 to indicate to the patient that the targeted temperature has been achieved or when the therapy has been completed.

The heating layer 36 may be configured to generate its heat energy, e.g., up to a temperature range of about 20° to 55° C. (or more) or between 40° to 50° C., through any number various mechanisms such as mechanical, electrical, or chemical mechanisms. In one variation, the heating layer 36 may comprise an air-activated warmer that can increase to an elevated treatment temperature for a period of time lasting, e.g., from 5 minutes up to 24 hours or even longer. An example can include air activated layer incorporating, e.g., iron. Other examples may incorporate a heating layer 36 containing, e.g., cellulose, iron powder, water, activated carbon (to speed up reaction), vermiculite (water reservoir), and salt (catalyst), saw dust, sodium chloride and water, etc. to generate heat from an exothermic oxidation of iron when exposed to air. Other variations may comprise a heating layer 36 which incorporates light-based activation (visible or UV-light powered) or use of a supersaturated solution (crystallization-type) to initiate and/or maintain an exothermic reaction.

Figure 3C:
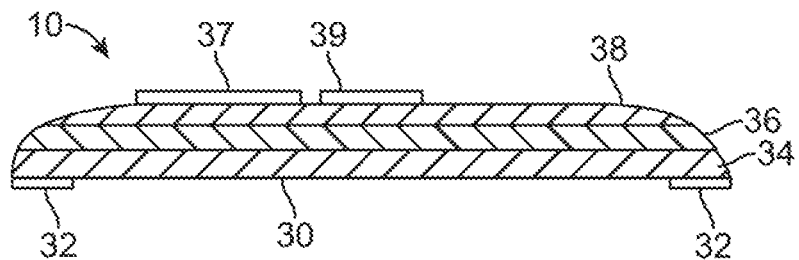
FIG. 3C shows another variation of a treatment strip which may optionally incorporate a controller.
Figure 3D:
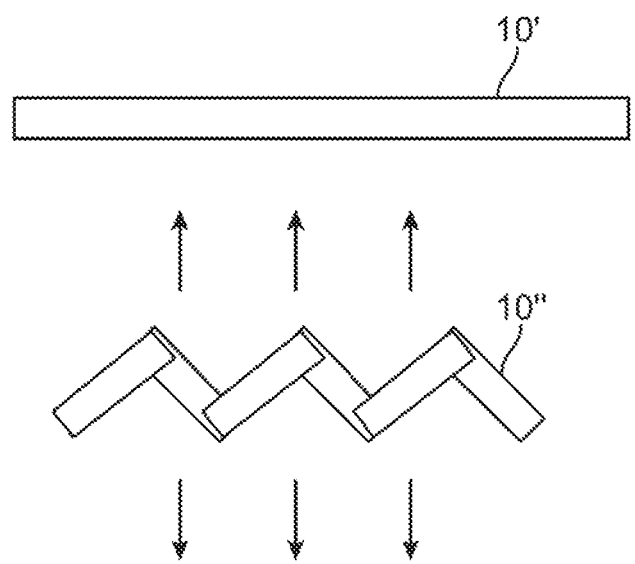
FIG. 3D shows yet another variation where a treatment strip may be formed into a zig-zag or curved configuration to facilitate the blinking by the patient.

Optionally, aside from use of a thermochromic material to determine when the treatment strip has reached a particular temperature, a separate temperature sensor 39 (e.g., thermocouples or thermistor devices) may be incorporated onto the treatment strip 10, as shown in FIG. 3B, attached either to the top of the strip or to the bottom of the strip. The treatment strip 10 may also incorporate an optional controller and/or display 37 having a processor which may be programmable and which may incorporate a separate on/off feature, as shown in FIG. 3C. The temperature sensor 39 may be in communication with the controller 37 which may be programmed to regulate the temperature of the heating layer 36 and/or a length of time for a particular treatment. The controller 37 may accordingly be programmable by a physician or caregiver or directly by the patient. Alternatively, the controller 37 may be configured to be inaccessible by the patient but may merely provide temperature and/or time indications for display to the patient. In the event that the controller 37 is programmable, the controller 37 may be programmed, e.g., to set a length of a heating period, set treatment times, set predetermined temperature ranges, control a heating temperature profile (such as gradually increasing the heating temperature or decreasing temperature over a predetermined period of time), etc.

In another variation, the heating layer 36 may generate heat through exothermic crystallization of supersaturated solutions (typically sodium acetate) which are usually reusable. The treatment strips may be recharged by heating them, e.g., by boiling, and allowing them to cool. Heating of these treatment strips may triggered by snapping a small metal device buried in the treatment strips which generates nucleation centers that initiate crystallization. Heat is required to dissolve the salt in its own water of crystallization and it is this heat that is released when crystallization is initiated.

In yet another variation, the heating layer 36 may comprise a battery operated warmer which utilizes electrically resistive heating elements that are used to convert electrical energy in the battery to thermal energy. The power supply may be internal or external to the treatment strips and the treatment strips may charged, e.g., by direct electrical contact, induction, etc.

Other mechanisms which may be incorporated into the heating layer 36 may comprise chemically actuated reactions such those used by sodium acetate heating pads. For instance, a single-use chemical reaction utilizing the catalyzed rusting of iron or dissolving calcium chloride may be use where the reagents are maintained in separate compartments within the treatment strips. When the patient squeezes the treatment strips, the compartments may break and the reagents mixed to produce heat. Examples may include use of a supersaturated solution of sodium acetate ($NaCH_3COO$) in water where crystallization may be triggered by flexing a small flat disc of notched ferrous metal embedded in the liquid which act as nucleation sites for the crystallization of the sodium acetate into the hydrated salt (sodium acetate trihydrate). Because the liquid is supersaturated, this makes the solution crystallize suddenly which releases the energy of the crystal lattice.

Yet another example of use in the heating layer 36 may include the use of a hot gel containing a supersaturated solution of a salt. Heat may be generated when the crystallization of the given salt occurs exothermically. Such heating layer 36 may be reused by forcing the salt back into solution within the heating layer 36.

Yet other examples for incorporation into the heating layer 36 may also include the use of high specific heat capacity materials which may be heated, e.g., by placement in a microwave prior to use, and then allowed to release the heat over a specified period of time.

Although the application of heat energy from the treatment strips is described, other variations may alternatively include the application of using the treatment strips for cooling of the underlying skin. Rather than using the heating layer 36 in an exothermic reaction, the layer may be configured to utilize an endothermic reaction instead to provide for cooling of the skin at temperatures ranging, e.g., from about 0° C. to 37° C. or more particularly from about 25° C. to 35° C. One example may include having the layer 36 to incorporate water and ammonium nitrate or ammonium chloride. Mixture of the water and the ammonium may reduce the temperature of layer 36. Another variation may include the use of cooling gel made by adding hydroxyethyl cellulose or vinyl-coated silica gel which may be cooled or frozen prior to use. Alternatively, cooling may be achieved by application of a cooling element such as a Peltier junction. Cooling, rather than heating, may be applied for conditions such as reducing inflammation, alleviating allergies or tired eyes, etc. particularly as the patient rests or sleeps. One example includes treatment for allergic conjunctivitis where application of the cooling treatment may provide relief from any burning or itching sensations by serving as a vasoconstrictor to limit blood flow, reduce blood vessel leakage and permeability thereby reducing acute swelling and inflammation. Yet another example includes reducing inflammation and fibrosis of a conjunctival bleb resulting from a trabeculectomy or mitigating inflammation generally following any ophthalmic surgical procedure.

Given the multitude of various mechanisms for incorporating a heating layer 36, the treatment strips may be configured to be single-use disposable strips, multiple-use disposable, re-usable strips, selectively actuatable, etc.

Aside from the application of heat energy from the treatment strips, the strips may also include a layer for the diffusion or release of one or more pharmaceutical, biological, or chemical agents either alone or in combination with the heat treatment. For instance, the pharmaceutical, biological, or chemical agents may be incorporated into the either the contact layer 34, insulative layer 38, or in a separate layer entirely, for transdermal delivery to the meibomian glands or to the areas surrounding the meibomian glands for additional and/or alternative treatments. For instance, examples of some of the various pharmacological agents which may be incorporated into the treatment strips (for use with or without the heat treatment) may include, but are not limited to, anti-inflammatory compounds, antibiotics, topical tetracycline, oral tetracycline, topical corticosteroids, oral corticosteroids, topical androgens, metronidazole, steroid antagonists, topical androgen analogues, TGF-β, omega 3 or omega 6 compounds, vasoconstrictors such as naphazoline, oxymetazoline, phenylephrine, and tetrahydrozoline, enzymes that promote lipid production, agents that stimulate production of enzymes that promote lipid production, agents that act as a secretagogue to enhance meibomian gland secretion, agents that replace or promote production of any tear component, cholinergic, muscarinic, or nicotinic agonists may be used, cosmeceuticals such as retinol or hyaluronic acid (HA) for wrinkled, puffy, or sagging skin in the cosmetics space, retinoic acid for acne, or agents that degrade or break down lipids like lipases, etc.

Other agents may include, e.g., alpha-melanocyte-stimulating hormone or adrenocorticotropic hormone or androgens like testosterone to increase tear production, agents which stimulate the underlying muscles like the orbicularis oculi or muscle of Riolan to stimulate blinking, increase frequency of blinking, or maintain longer closure after a blink by inhibiting the levator palpebrae muscle to force a blink or eyelid closure or otherwise mechanically compress the meibomian glands or glands of Zeis or other goblet cells or accessory lacrimal glands.

Additionally and/or alternatively, other agents for incorporation into the treatment strips may further include, e.g., neurotransmitters, noxious or irritating chemicals or vapors, hormones, oils, lipids, polar lipids, or fatty acids. Use of neurotransmitters may allow for stimulation to occur via second messenger pathways like activation of the Calcium/Protein Kinase C pathways, G-Protein activation, other calcium related pathways, calcium-calmodulin dependent protein kinases, the cyclic adenosine monophosphate dependent pathways, adenylyl cyclase pathways, inhibition of cAMP dependent phosphodiesterases.

In the event that the pharmacological or chemical agent is released during the heat treatment, the heat may help to improve penetration of any drugs into the underlying skin.

Yet another variation may incorporate a treatment strip which applies a heat rub that can be applied via the treatment strips onto the upper UL and/or lower eyelids LL for the treatment of the meibomian glands or which applies a compound which attracts light and heats up accordingly. Each of these variations may allow for the treatment strips 10, 12 to be applied and used while allowing for natural blinking to occur to facilitate the clearing of the ducts of melted oil blockages within the meibomian glands and to facilitate the spreading of the oil onto the tears.

Figure 4:
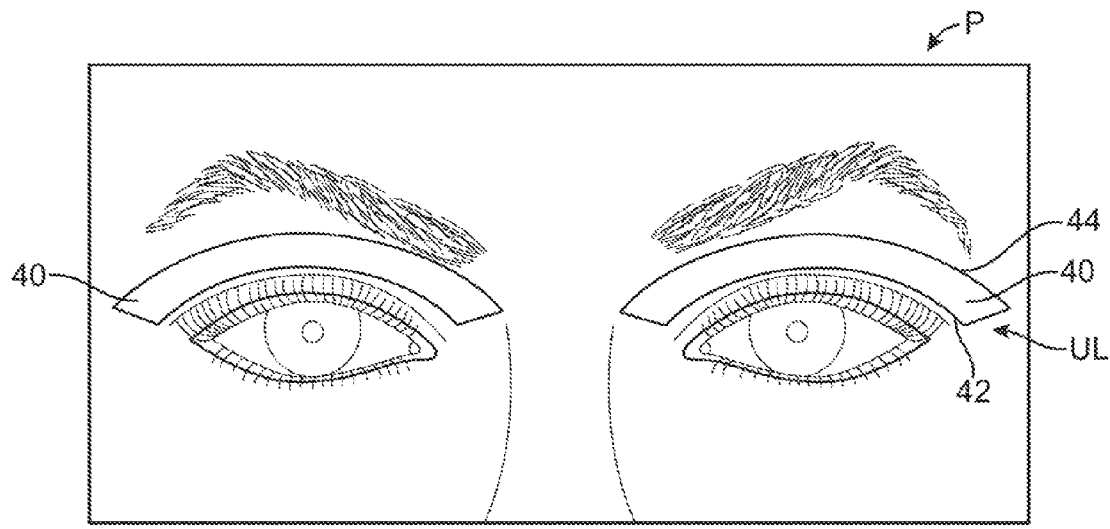
FIG. 4 shows a front view of another variation of the treatment strip which is relatively thin and positioned over the upper eyelids.

While the treatment strips may incorporate various layers into the strips to effect various different treatments, the strips may also be varied in size, shape, contour, etc. depending upon the desired treatment areas so long as the treatment strips are contoured or shaped to follow the location of at least one meibomian gland. An example of another configuration for the treatment strips is shown in the front view of FIG. 4, which illustrates a contoured thinned strip 40 sized and shaped for placement along the upper eyelid UL. This treatment strip may have a contoured lower edge 42 as well as a contoured upper edge 44 which follow the positioning of the underlying meibomian glands. Moreover, although the strips 40 are shown placed upon the upper eyelids UL of both eyes of the patient P, a single strip 40 may be used upon a single eyelid to selectively treat the particular meibomian glands in this and other examples shown herein. Additionally, one or both upper eyelids UL may be treated alone or in combination with one or both lower eyelids LL depending upon the desired treatment in this and other examples shown herein.

Figure 5:
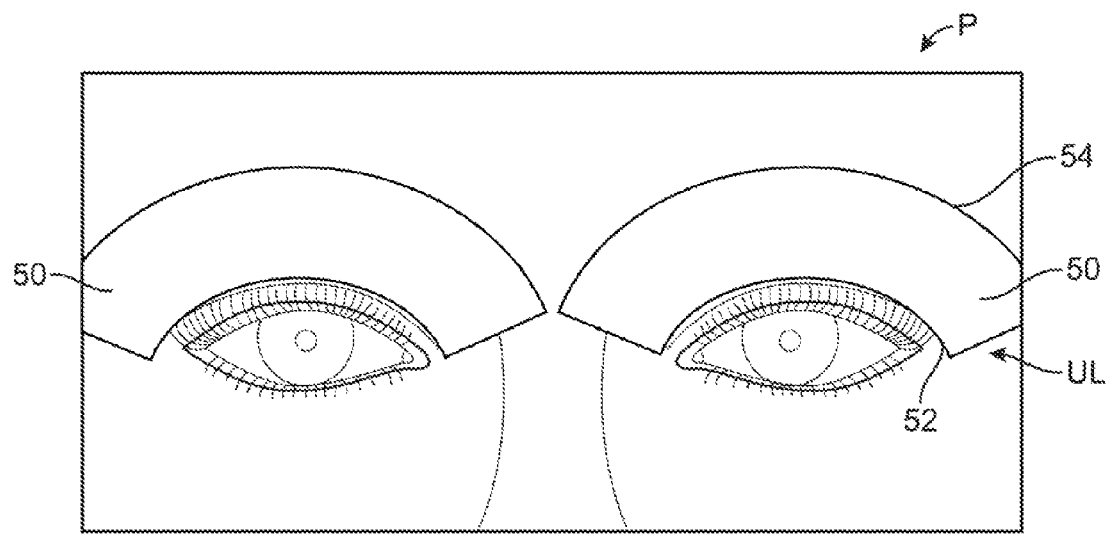
FIG. 5 shows a front view of another variation of the treatment strip which is relatively thick for treatment of the targeted meibomian glands as well as the surrounding tissue.

Another variation is shown in the front view of FIG. 5 which shows a contoured thickened strip 50 having a contoured lower edge 52 and contoured upper edge 54 for placement upon the meibomian glands as well as the surrounding tissue and glands. In yet other variations, rather than utilizing two separate treatment strips, a singular strip may also be used which extends over the bridge of the patient's nose. Additionally, the thickened strip 50 may cover the portions of skin farther proximally away from the eyelid margin to facilitate treatment. Because arterial blood supply to the eyelids proceed from proximal to distal of the eyelid margins, the treatment strip may heat (or cool) the blood supply as it continues to flow towards the eyelid margins. This early heating (or cooling) may provide a therapeutic effect for increased comfort to the patient, less impact on eyelid function (such as blinking), and increased safety of application and distance from the ocular surface as well as potentially increased efficacy allowing for more total heating or cooling therapy.

Figure 6:
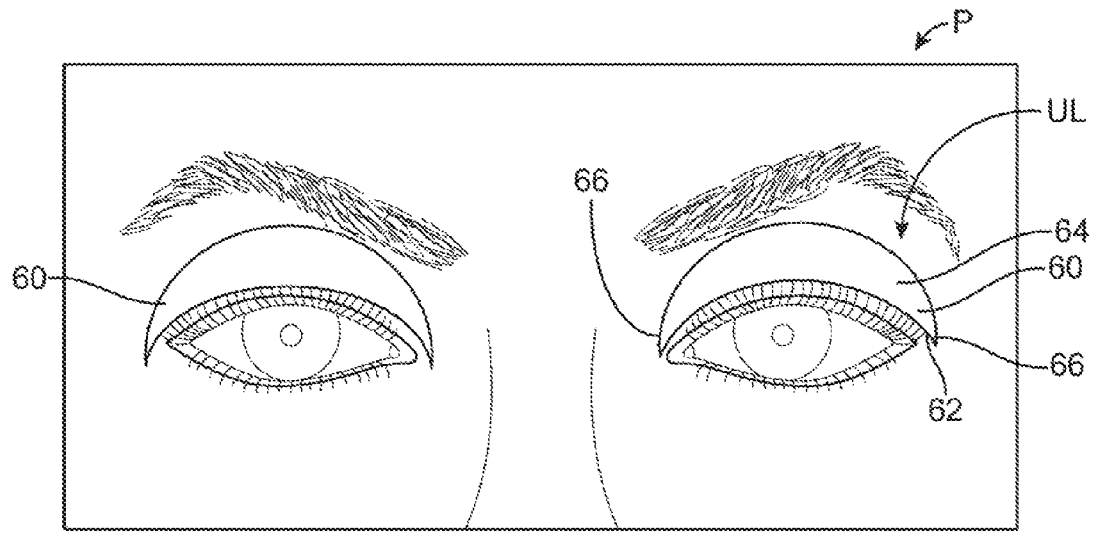
FIG. 6 shows a front view of another variation of the treatment strip which is contoured to more closely follow the meibomian glands in the upper eyelids.
Figure 7:
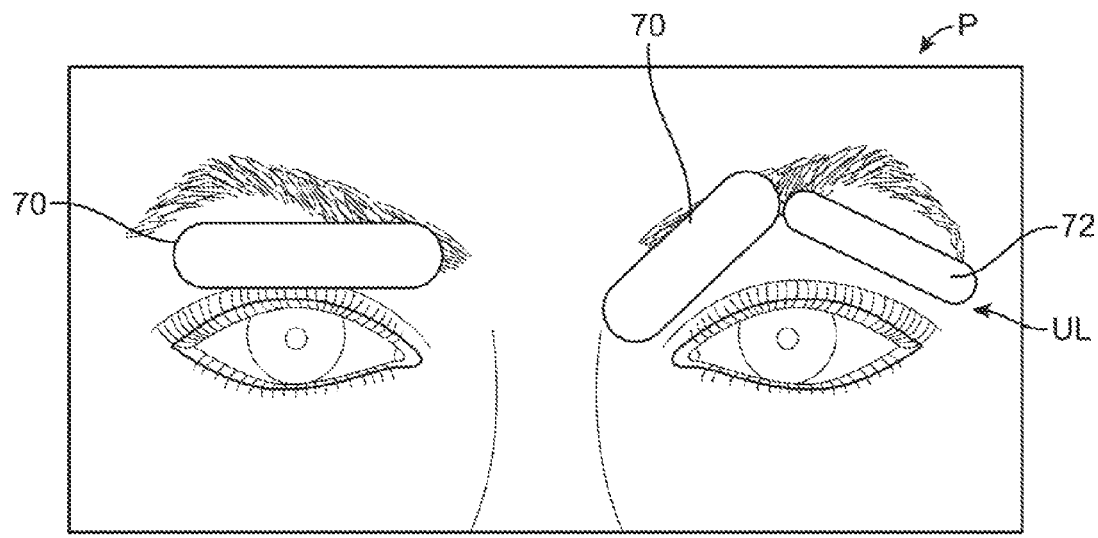
FIG. 7 shows a front view of another variation of the treatment strip which may be formed into shortened strips for selective placement along the eyelids.

FIG. 6 shows yet another variation having a contoured thinned strip 60 where the lower 62 edge and upper edge 64 converge to a tapered end 66 for placement upon the meibomian glands. FIG. 7 shows yet another variation where the treatment strips may comprise straightened strips 70 having a first width used in combination with a thinned straightened strip 72 as well. The straightened strips 70 may comprise straightened strips (having optionally rounded corners) which may be selectively placed over the meibomian glands. In this example, a single straightened strip 70 may be applied upon the upper eyelid UL of a single eye while the remaining eye may utilize a single straightened strip 70 applied along a first portion of the upper eyelid UL and a second straightened strip 72 having a relatively thinner width for placement upon a second portion of the upper eyelid UL. Each of the strips may be applied singularly or in various combinations depending upon the desired treatment areas and are shown in this variation as an exemplary combination.

Figure 8:
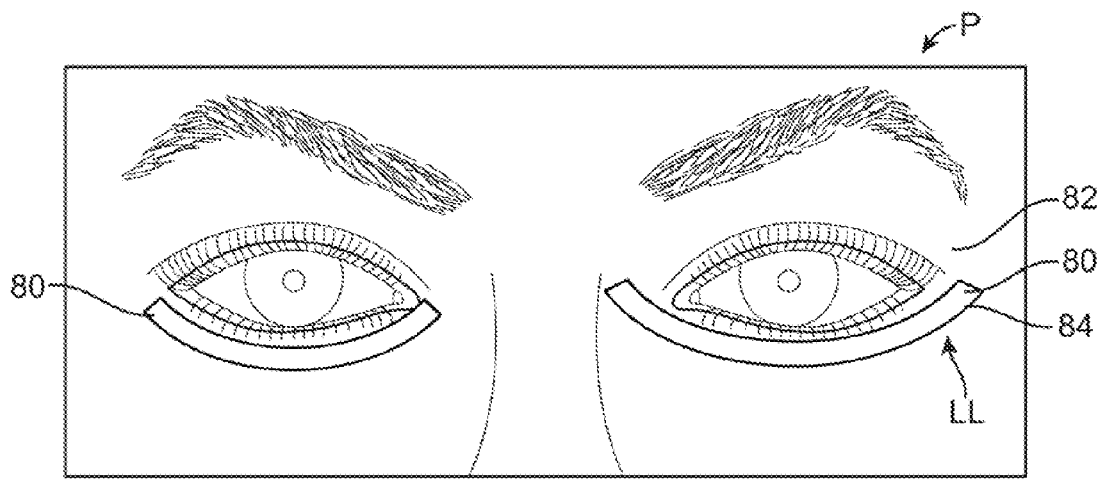
FIG. 8 shows a front view of another variation of the treatment strip which is relatively thin and contoured for placement along the lower eyelids.

In the variation of FIG. 8, an example of contoured thinned strip 80 is shown applied along the lower eyelid LL. As illustrated, the contoured upper edge 82 and contoured lower edge 84 may be contoured to follow over the underlying meibomian glands. As described above, the treatment strips may be applied singularly over one or both eyes or they may be applied in combination with treatment strips applied over one or both eyes of the upper eyelids. Moreover, any of the treatment strips shown herein may be used in any number of combinations with one another.

Figure 9:
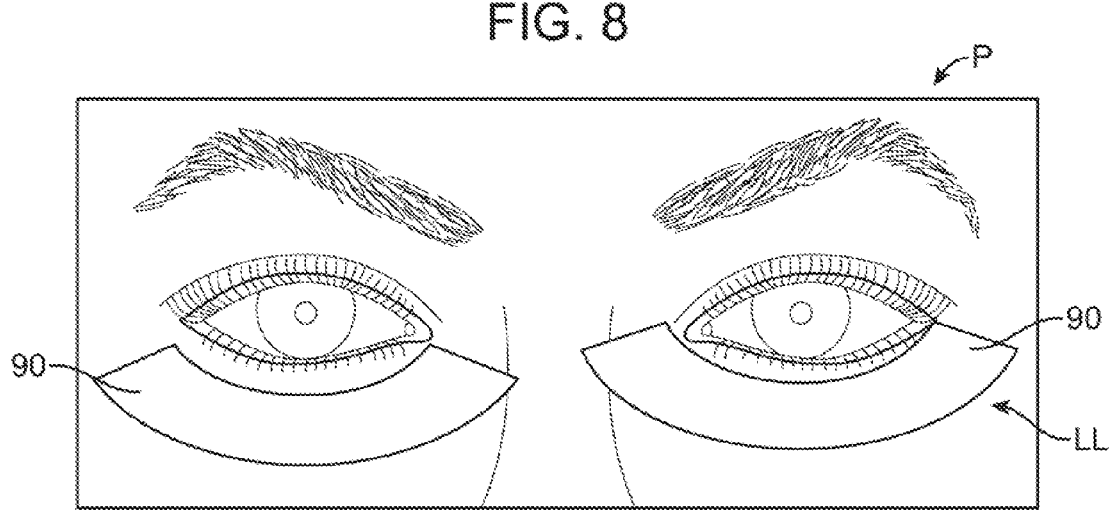
FIG. 9 shows a front view of another variation of the treatment strip which is relatively thicker and also contoured for placement along the lower eyelids.
Figure 10:
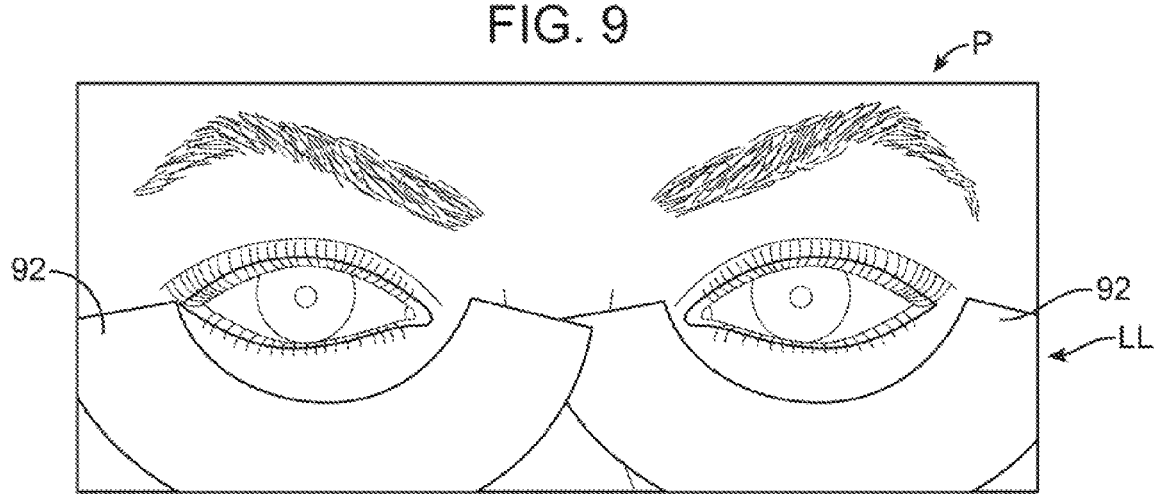
FIG. 10 shows a front view of another variation of the treatment strip which is relatively thick for placement along the lower eyelids.

FIG. 9 shows another variation where the contoured thickened strip 90 may be applied over the lower eyelids LL and may further have a width which is relatively wider than those treatment strips shown above in FIG. 8. Similarly, FIG. 10 shows yet another variation where the contoured thickened strip 92 may have a width which is relatively wider still for treating not only the underlying meibomian glands but also any glands and tissue surrounding the peri-orbital region. As described above for the variation of FIG. 5, the widened treatment strip may heat (or cool) the blood supply as it continues to flow towards the eyelid margins. The early heating (or cooling) may provide a therapeutic effect for increased comfort to the patient, less impact on eyelid function (such as blinking), and increased safety of application and distance from the ocular surface.

Figure 11:
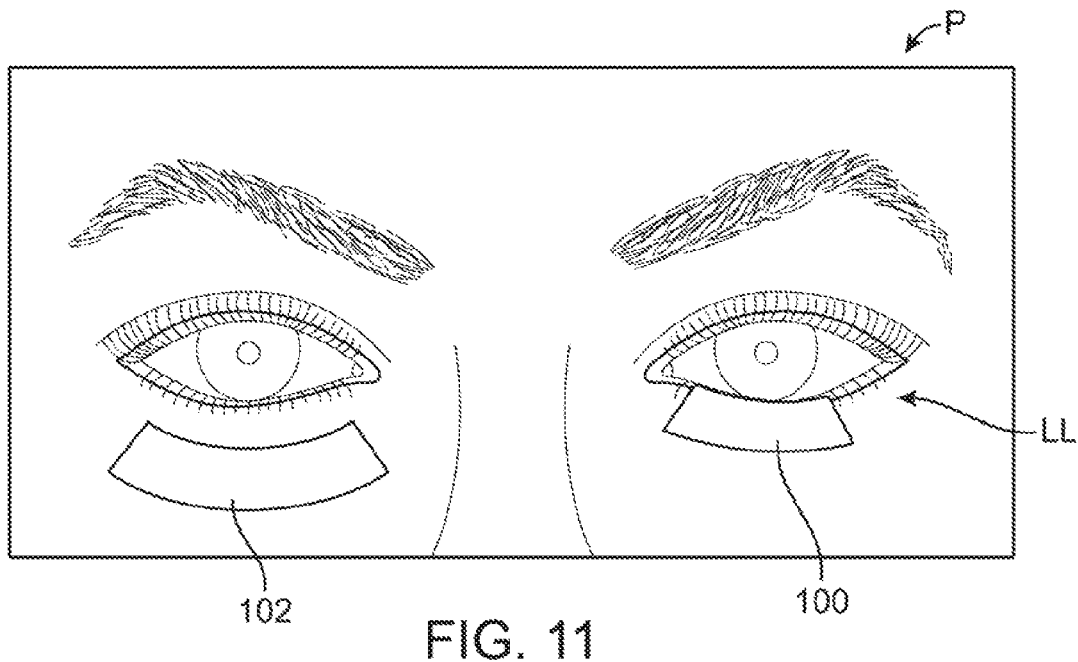
FIG. 11 shows a front view of another variation of the treatment strip which is contoured for the lower eyelids and which may be shortened into various lengths.
Figure 12:
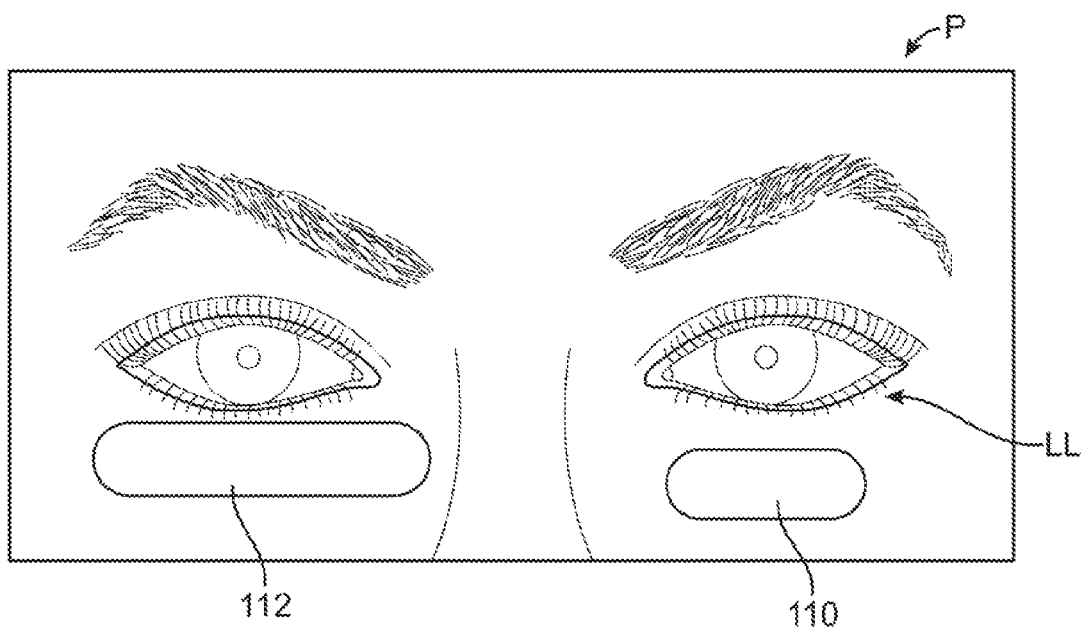
FIG. 12 shows a front view of another variation of the treatment strip which is relatively straightened and selectively shortened.

Aside from variations in width of the treatment strips, any of the treatment strips may be varied in length as well to selectively target portions of the meibomian glands or particularly selected meibomian glands. For example, FIG. 11 shows one variation where the shortened contoured strip 100 having a first shortened length may be applied upon the lower eyelid LL (and/or upon the upper eyelid UL). A second contoured strip 102 having a second length which is longer than the shortened contoured strip 100 may also be seen for comparison. FIG. 12 similarly shows a shortened and straightened strip 110 applied upon the lower eyelid LL and a second straightened strip 112 having a relatively longer length applied upon the second lower eyelid LL. The straightened strips 110, 112 may incorporate rounded ends and may be varied in length depending upon the desired treatment area. They could also be rounded or circular to cover one or more styes.

Figure 13:
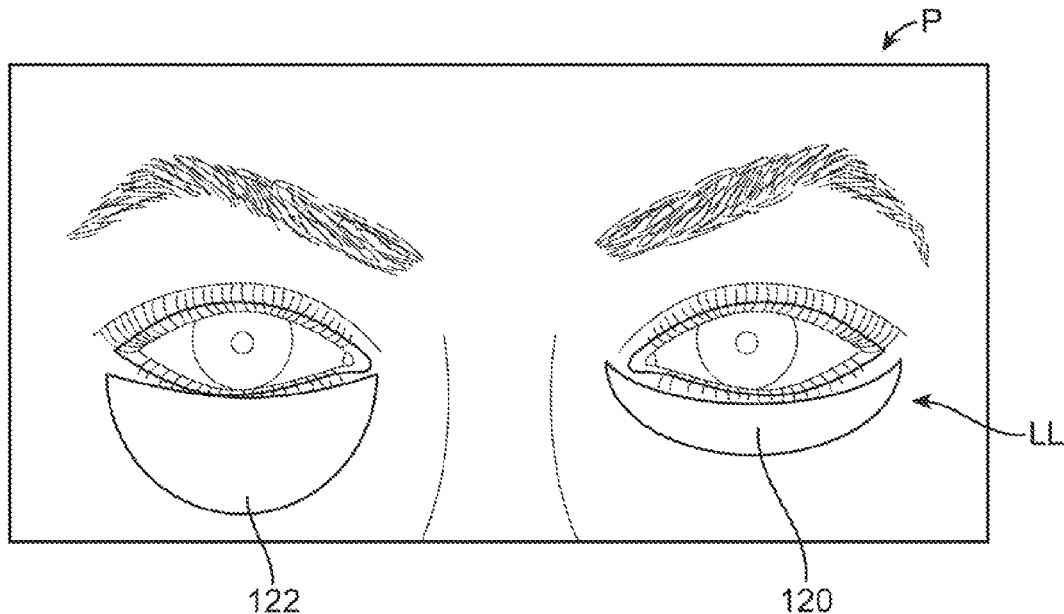
FIG. 13 shows a front view of another variation of the treatment strip which is contoured and further illustrates how differently sized strips may be used in combination with one another.

FIG. 13 shows yet another variation where the contoured strips 120 may be configured to have tapered ends for overlying the meibomian glands. In comparison, thickened contoured strip 122 is also illustrated having tapered ends yet is relatively wider to alter the treatment area.

Figure 14:
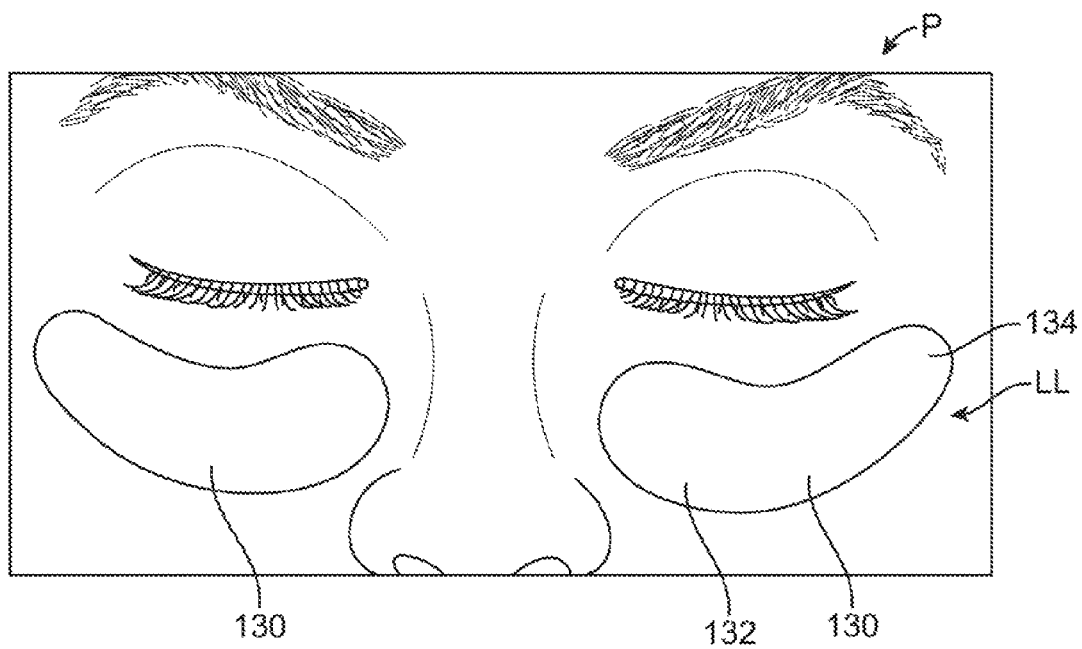
FIG. 14 shows a front view of another variation of the treatment strip which is sized to follow not only the meibomian glands along the lower eyelid but also the surrounding tissue regions.
Figure 15:
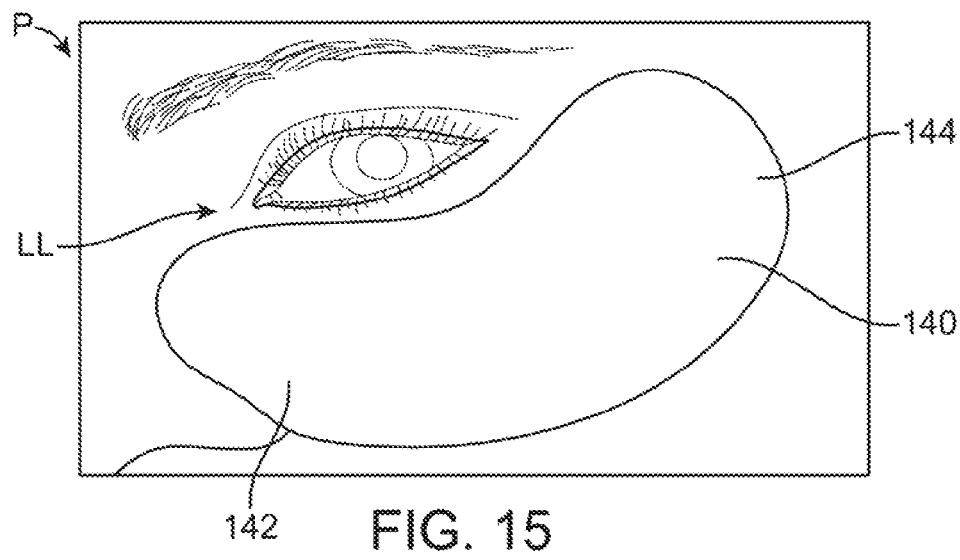
FIG. 15 shows a front view of another variation of the treatment strip which is contoured to follow the meibomian glands along the lower eyelid along with the surrounding tissue regions.
Figure 16:
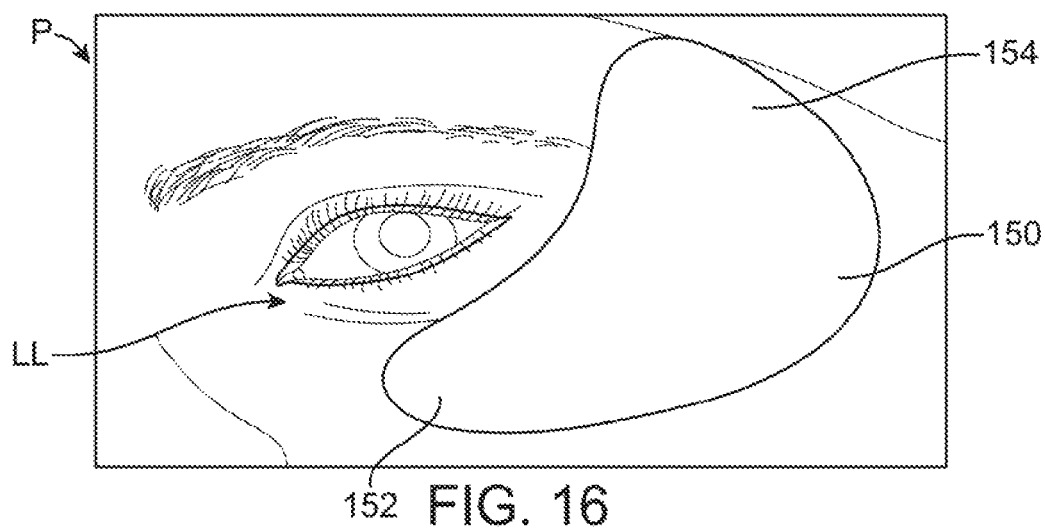
FIG. 16 shows a front view of yet another variation where the strip is contoured to follow at least a portion of the meibomian glands but also to cover selected regions of the surrounding tissue.

FIG. 14 shows another variation where the contoured strip 130 may have a first portion 132 which is relatively wider than a second portion 134 for placement over the meibomian glands of the lower eyelid LL. Each of the first 132 and second portions 134 may be varied in width again depending upon the desired treatment areas. Another example is shown in FIG. 15 which shows a contoured strip 140 having a first portion 142 and second portion 144 which are considerably wider for treating not only the meibomian glands along the lower eyelid LL but also the surrounding peri-orbital tissue regions such as the underlying maxillary sinus. FIG. 16 shows yet another example of a contoured strip 150 having a first portion 152 and a second portion 154 which is wider than the first portion 152 and where the strip 150 is positioned to cover just a portion of the meibomian glands along the lower eyelid LL but also covers various other glands, such as the lacrimal glands, around the peri-orbital regions.

Figure 17:
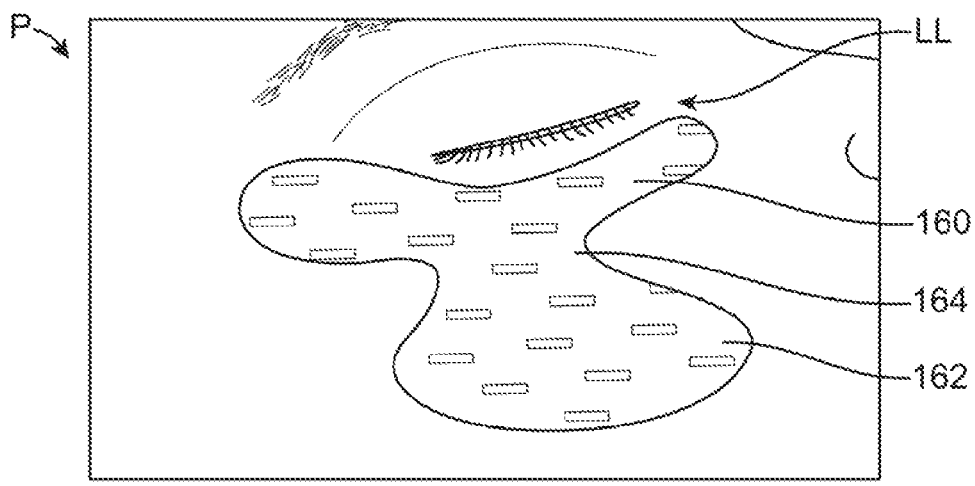
FIG. 17 shows a front view of yet another variation which is contoured to selectively treat particular regions of the underlying tissue.

FIG. 17 shows yet another variation of a treatment strip comprised of a contoured strip 160 having a secondary enlarged portion 162 attached via a connecting strip 164. While the contoured strip 160 may treat the meibomian glands along the lower eyelid LL, the secondary enlarged portion 162 may treat region of the tissue along the cheeks of the patient.

Figure 18:
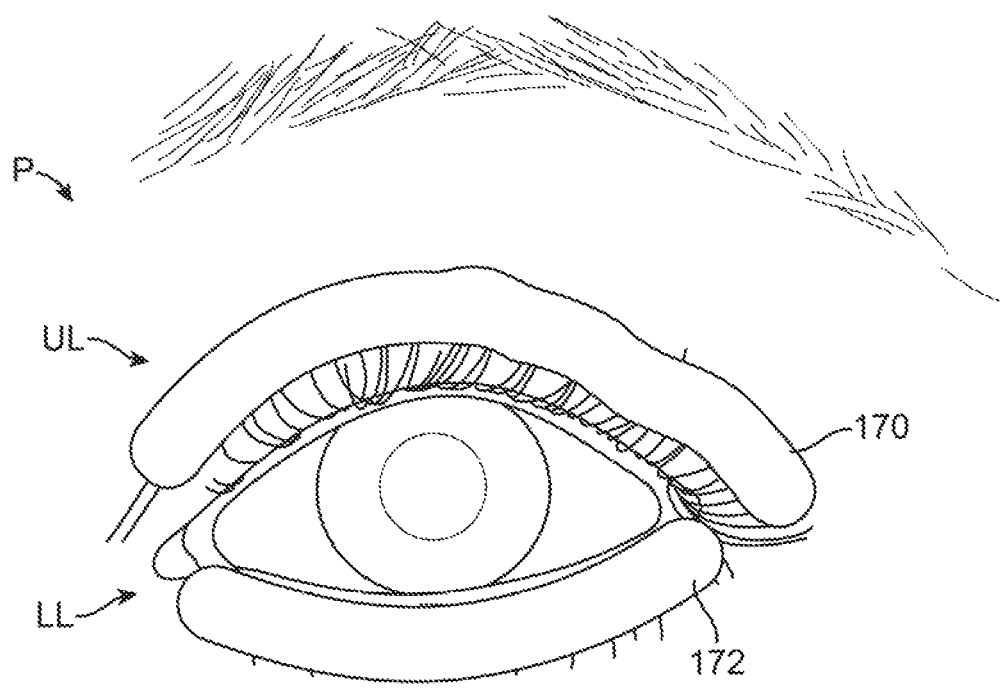
FIG. 18 shows a front view of yet another variation where the contoured treatment strips may be used in combination for treating both upper and lower eyelids.
Figure 19:
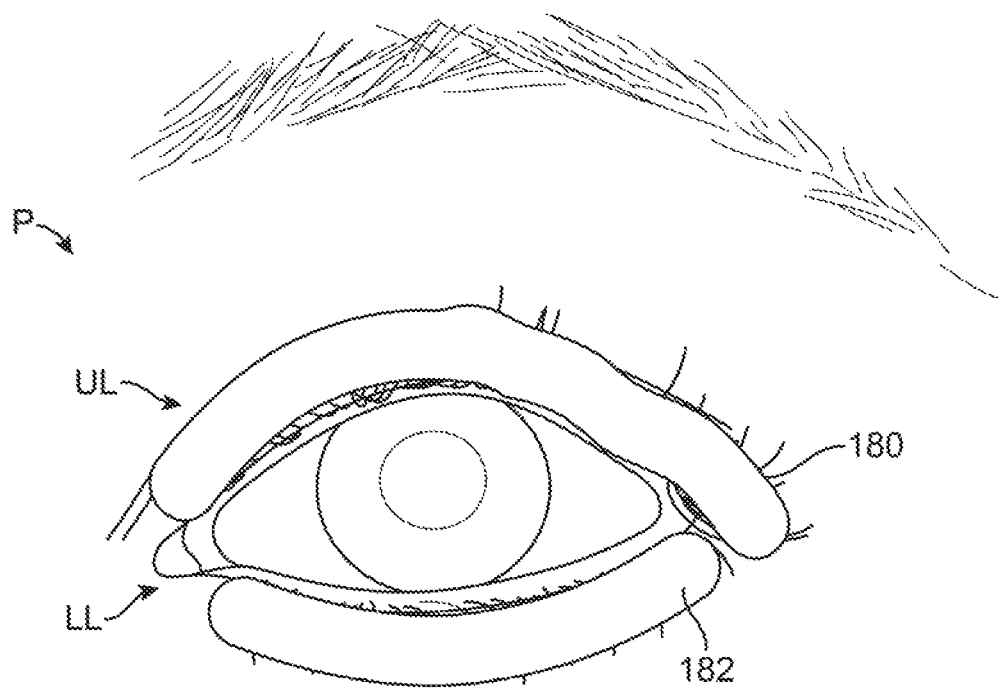
FIG. 19 shows a front view of yet another variation where the treatment strips may be altered in color to more closely match the underlying skin tone.

In yet another variation, FIG. 18 shows an example where both an upper contoured strip 170 and a lower contoured strip 172 may be applied, respectively, along the upper eyelid UL and lower eyelid LL. As discussed previously, the contoured strips 170, 172 are shaped and applied to follow the underlying meibomian glands while enabling the patient P to blink normally. FIG. 19 shows a similarly applied upper contoured strip 180 and lower contoured strip 182 where the strips may be varied in color to more closely match a skin tone or shade of the patient P. Because the treatment strips may be used throughout the day for any given period of time, the strips 180, 182 may be made in various colors or tones to either more closely match the skin tone or shade of the patient P.

Figure 20:
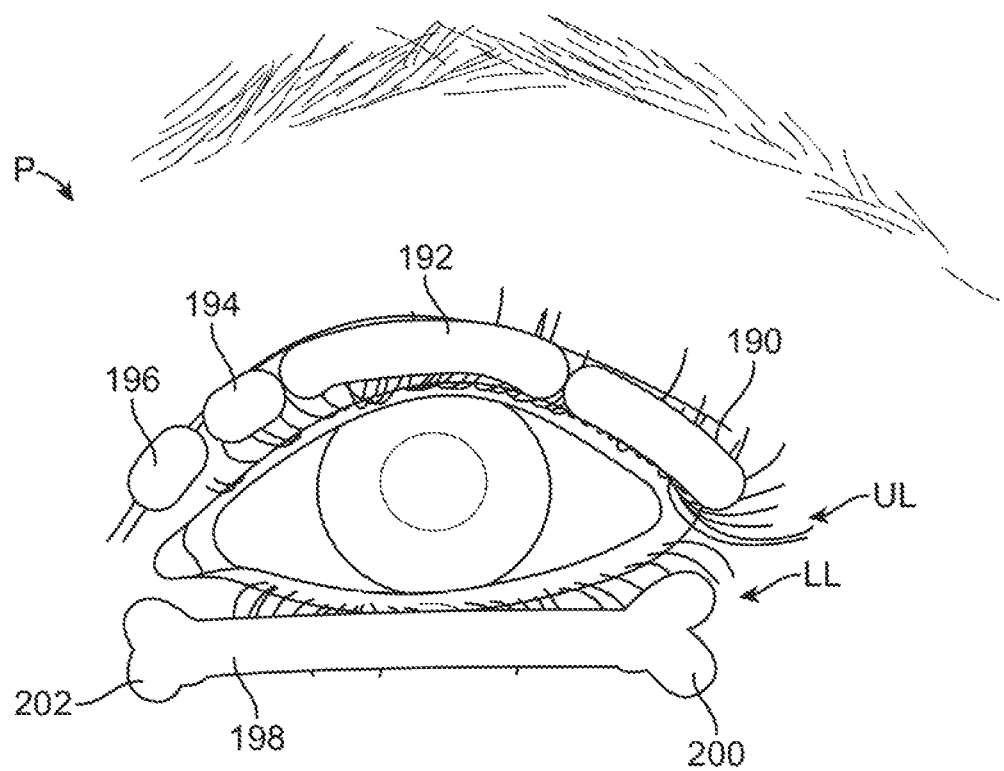
FIG. 20 shows a front view of yet another variation where the treatment strips may be sized to treat specified meibomian glands.
Figure 21:
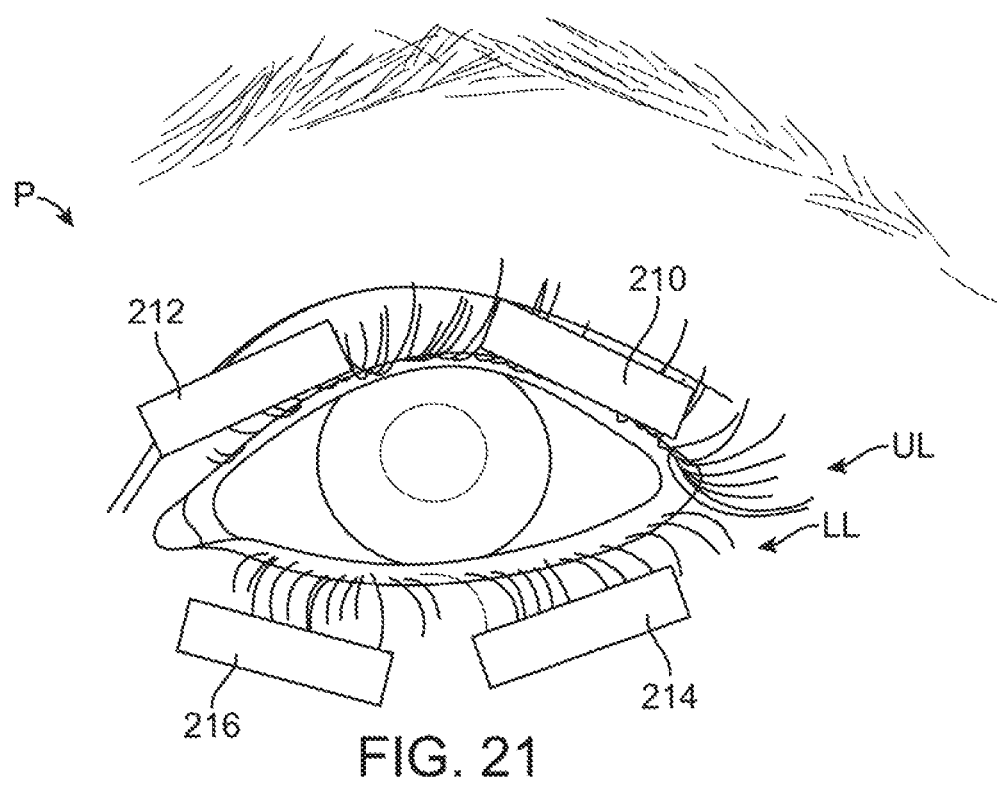
FIG. 21 shows a front view of yet another variation where the strips may be varied in size to selectively treat particular meibomian glands.

In yet another variation, FIG. 20 shows another example where the treatment strips may be varied in length to treat specific regions along the upper UL or lower eyelids LL. In this example, a first upper strip 190 having a first length may be applied adjacent to a second upper strip 192 having a second longer length. Optionally, a third upper strip 194 and/or fourth upper strip 196 having lengths which are relatively shorter may also be applied as well over selected meibomian glands. A lower strip 198 having enlarged distal ends 200, 202 are also shown for placement along the lower eyelid LL. The distal ends 200 may be shaped to facilitate the placement and/or removal of the strip 198 from the skin (or for better adhesion). Yet another example is shown in FIG. 21 which illustrates several shortened treatment strips, e.g., first upper strip 210 and second upper strip 212, placed selectively along the upper eyelid UL along with, e.g., first lower strip 214 and second lower strip 216, placed selectively along the lower eyelid LL. Each of the strips may be varied in length as well as size depending upon the treatment area.

Figure 22:
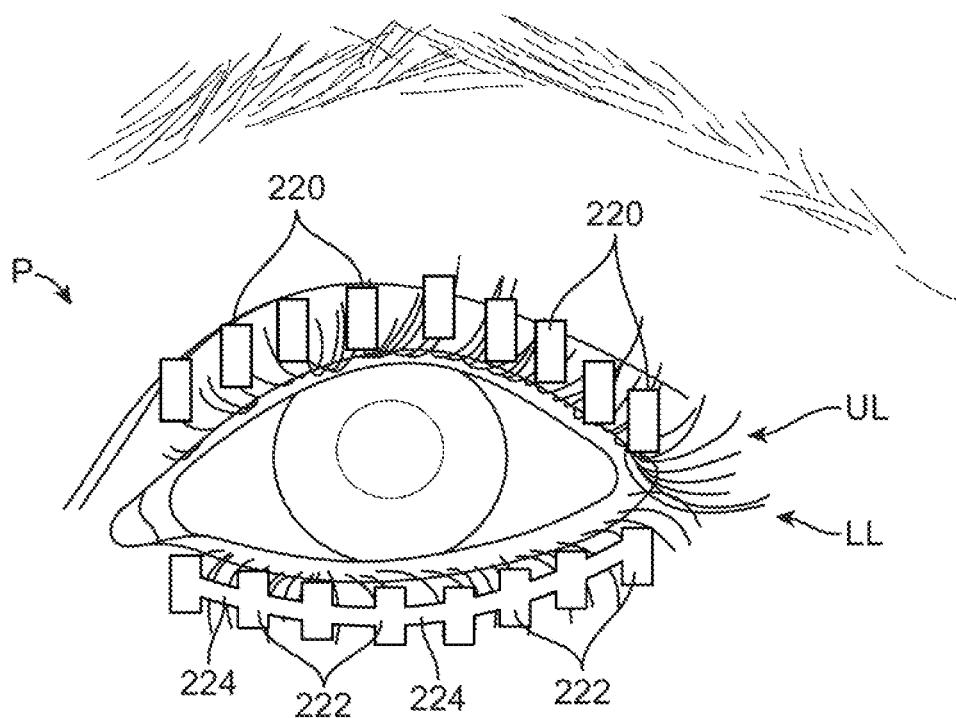
FIG. 22 shows a front view of yet another variation where the treatment strips may be sized to treat individual meibomian glands.
Figure 23:
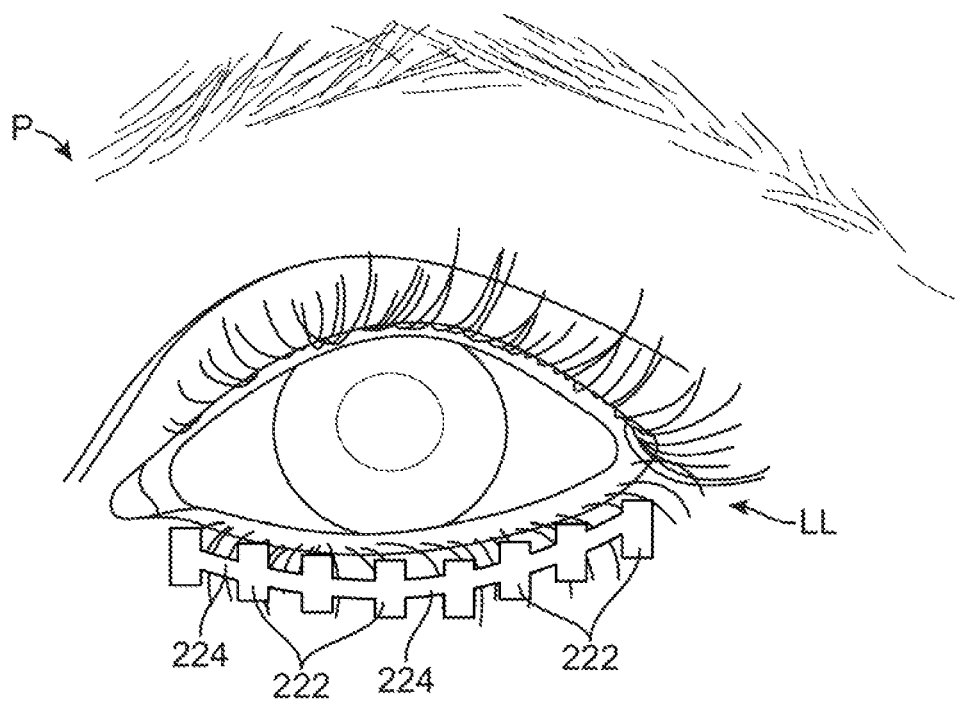
FIG. 23 shows a front view of yet another variation where the treatment strips may be sized for placement along the lower eyelids.

With the lengths of the treatment strips being variable, multiple strips may be applied adjacent to one another or to overlap horizontally and/or vertically along the eyelids. Moreover, one or more of the treatment strips may be made as a single unit or as a series of panels either horizontally or vertically oriented which may be optionally connected by a backing that is flexible. As shown in the variation of FIG. 22, each of the targeted strips 220 may have a length of, e.g., about 1 mm, to cover as few as a single meibomian gland. One or more of the targeted strips 220 may be applied along the upper eyelid UL and/or lower eyelid LL. Additionally, one or more of the targeted strips 222 may further comprise a connecting member 224 which functions as a backing to couple each of the individual targeted strips 222 to one another. The individual strips may be applied selectively at particularly problematic meibomian glands either along the upper eyelid UL and/or lower eyelid LL. For example, FIG. 23 illustrates the individual targeted strips 222 placed along just the lower eyelid LL.

While the treatment strips may be applied to one or more of the meibomian glands, variations of the strip may also be used to treat other glands such as the sebaceous glands, e.g., for acne treatment. Treatment strips used to treat acne may utilize different pharmacological treatments. Other glands in the underlying eyelids and conjunctiva CN for treatment may also include treatment of, e.g., the glands of Zeis GZ, goblet cells, accessory sebaceous glands, accessory goblet cells such as the Henle and Manz glands, accessory lacrimal glands of Wolfring GW or Krause GK, or either one or both lobes of the main lacrimal glands such as the palpebral portion or the orbital portion.

Moreover, the treatment strips may be used to potentially treat eye disorders beyond meibomian gland dysfunction including, e.g., blepharitis, sjogren's syndrome, dacryoadenitis, conjunctivitis, allergic conjunctivitis, keratoconjunctivitis sicca, keratitis, dacryocystitis, iritis, keratitis, retinitis, sclerokeratitis, uveitis, contact lens related eye problems, post blepharoplasty or eyelid or eye surgical procedures (e.g., cataract surgery, LASIK, PRK, etc.), absent or dysfunctional blinks disorders, conjunctivitis, blepharospasm, exposure keratopathy, lagophthalmos, lid myokymia, infections, styes, chalazion, hordeolum, glaucoma, blebs, trauma, etc.

Figure 24:
FIG. 24 shows a front view illustrating the relative positioning of the lacrimal glands.
Figure 25:
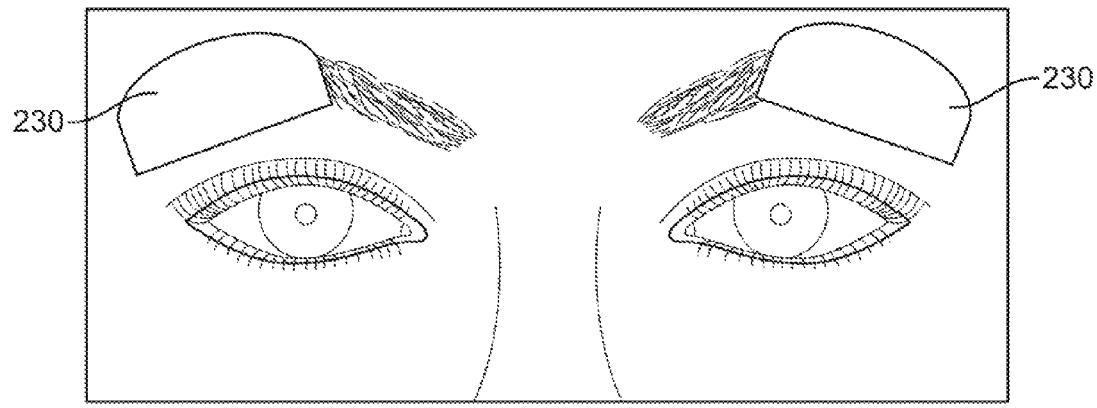
FIGS. 25 to 27 show variations of treatment strips which may be contoured and positioned for treating the underlying lacrimal glands.
Figure 26:
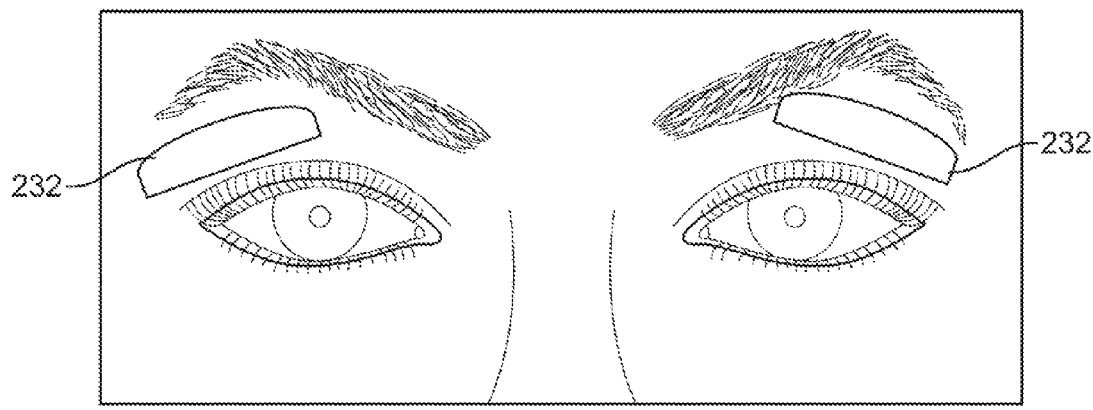
Figure 27:
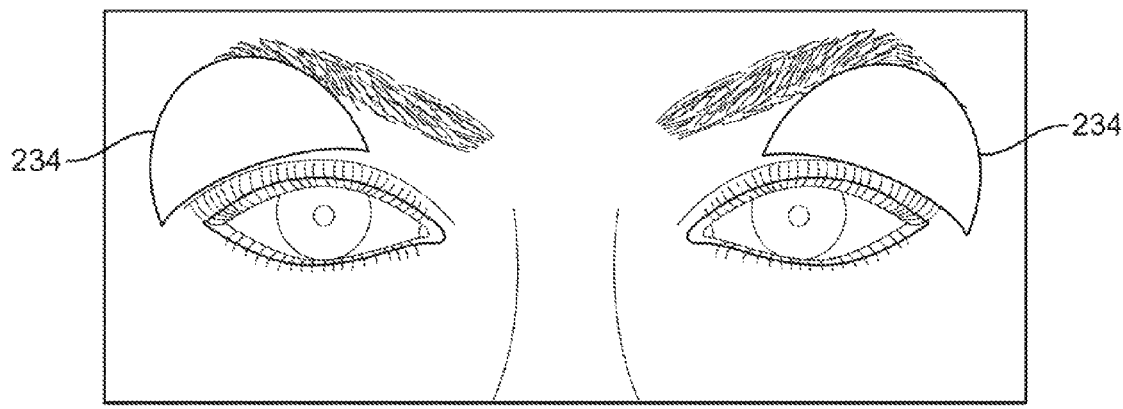

Yet another example, as mentioned above, may include use of the treatment strips for treating disorders of the lacrimal gland LG and/or palpebral lacrimal gland PL which are located above the eye as shown in FIG. 24. Variously sized treatment strips, such as lacrimal gland strips 230 shown in FIG. 25 which is sized to have a curved upper periphery, may be sized for placement directly over the skin surface above where the lacrimal glands LG are located. Other variations are shown in FIG. 26 which illustrates lacrimal gland strips 232 which are relatively thinner in width as well as in FIG. 27 which illustrates lacrimal gland strips 234 which have curved peripheries ending in tapered ends. The treatment strips may deliver heat, e.g., to stimulate the lacrimal gland LG, increase gland metabolism, activity, lacrimation, etc. Alternatively, the treatment strips may deliver cooling therapy to reduce inflammation which impairs gland function.

Figure 28:
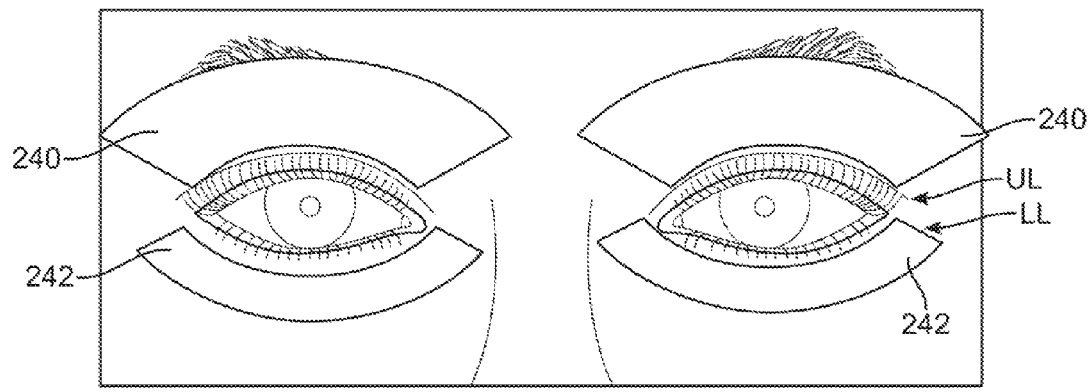
FIGS. 28 to 30 show variations of treatment strips which may be contoured and sized for treating the meibomian glands in combination with optionally treating the lacrimal glands as well.

The lacrimal glands LG and/or palpebral lacrimal gland PL may be treated alone or in combination with the treatment strips contoured for treatment of the meibomian glands. One variation is shown in FIG. 28 which illustrates contoured strips 240 which are enlarged in width to cover both the lacrimal glands LG as well as the meibomian glands along the upper eyelid UL. Contoured treatment strips 242 are also shown placed along the lower eyelids LL for treatment of the meibomian glands as well.

Figure 29:
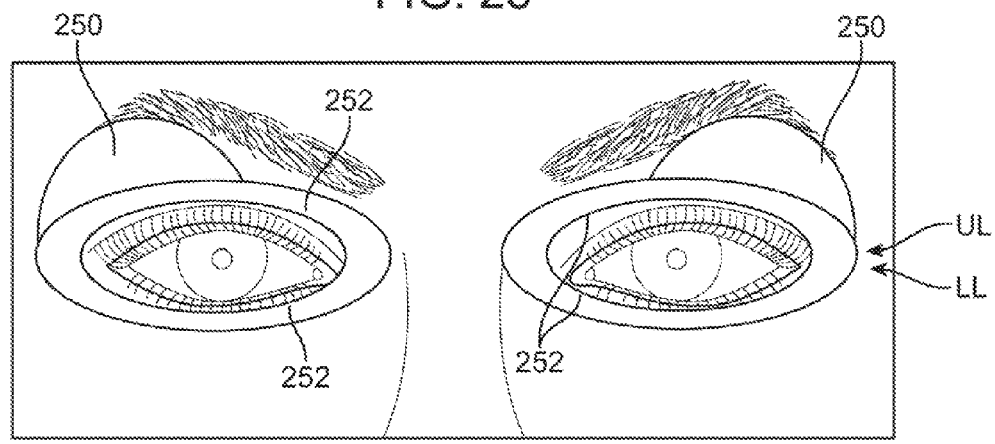
Figure 30:
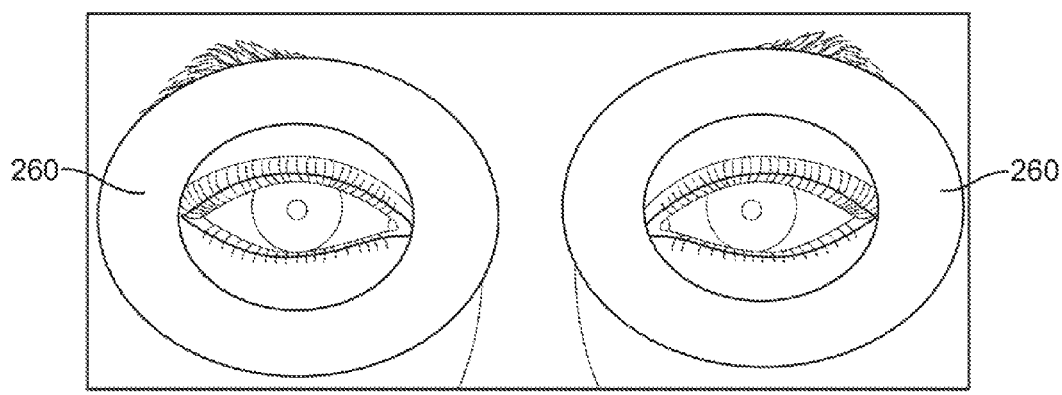

FIG. 29 shows another variation where lacrimal gland strips 250 may be placed over the lacrimal glands LG in combination with an integral combined contoured strip 252 which is sized to encircle the eyes entirely while following the location of the meibomian glands along both the upper eyelids UL and lower eyelids LL. This fully encircling design may also be held in place more tightly against the skin with a strap which may encircle the patient's head, if so desired. Another variation is shown in FIG. 30 which illustrates an integral combined contoured strip 260 which is also sized to encircle the eyes entirely and further having a width suitable for placement over the lacrimal glands LG.

Figure 31:
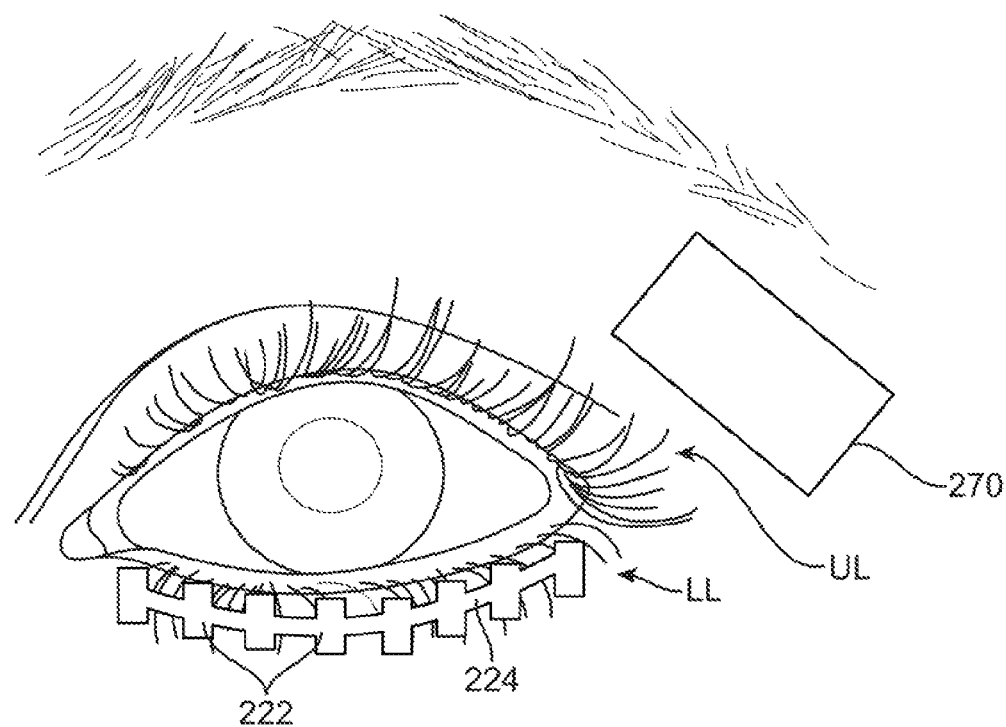
FIGS. 31 and 32 show variations on treatment strips which may be sized for selectively treating particular meibomian glands in combination with the lacrimal gland.
Figure 32:
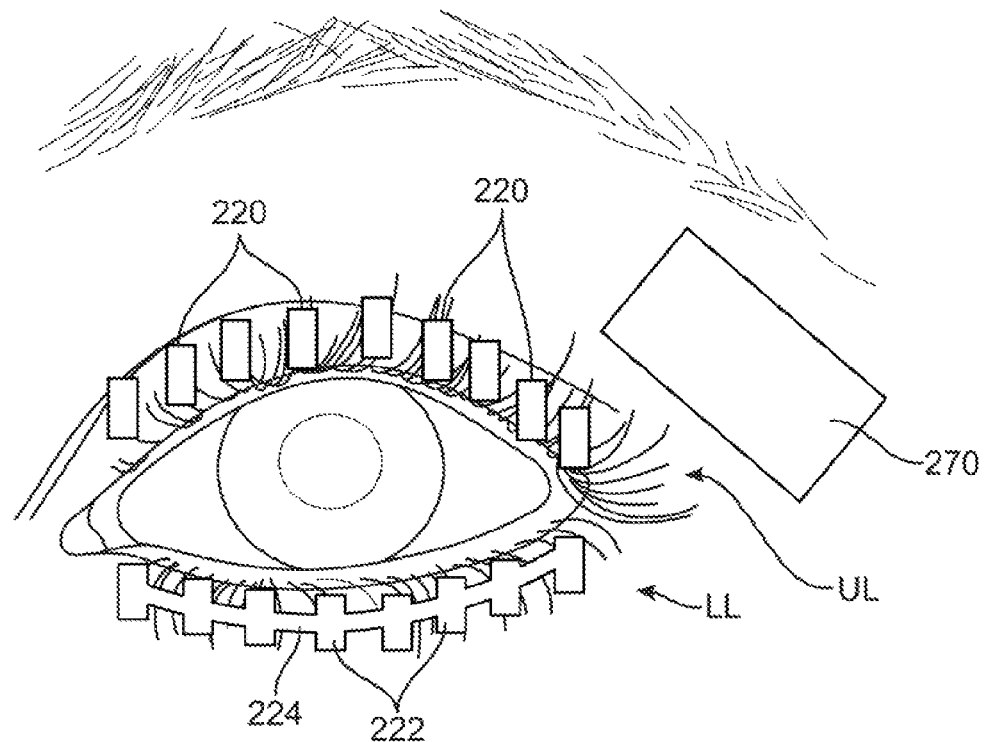

The lacrimal gland strip 270 may be used in combination with any of the treatment strips shown herein. Another example is illustrated in FIG. 31 which shows lacrimal gland strip 270 used in combination with the individual strips 222 while FIG. 32 shows yet another example where lacrimal gland strip 270 may be used in combination with not only the individual strips 222 but also the strips 220 located along respective lower eyelid LL and upper eyelid UL.

Figure 33:
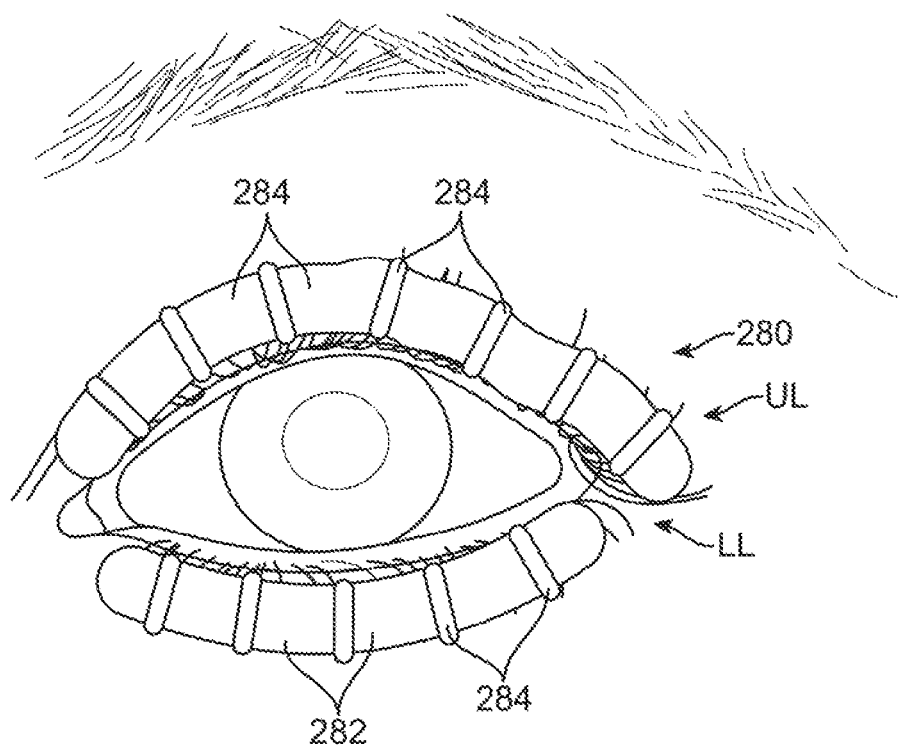
FIG. 33 shows another variation of a treatment strips which may have mechanically biasing features incorporated along the strips for applying a force to the underlying tissue and meibomian glands.

While the treatment strips may be applied over the meibomian glands to apply the heat energy, the treatment does not require the application of any external force applied by the strip or any other external device but may utilize the natural blinking of the patient to facilitate treatment, as described above. However, in additional variations, the treatment strips may be configured to apply both the heat treatment as well as an external force. Any number of mechanisms may be utilized to apply a pinching or biasing force to provide for compression of the underlying skin and of the meibomian glands during application of the heat therapy. One example is shown in the front view of FIG. 33 which illustrates a biased treatment strip 280 which may be comprised of a strip 282, as previously described, having one or more biasing mechanisms 284 positioned along the strip 282. The one or more biasing mechanisms 284 may be positioned along either the upper strip or lower strip or both, as shown.

Figure 34:
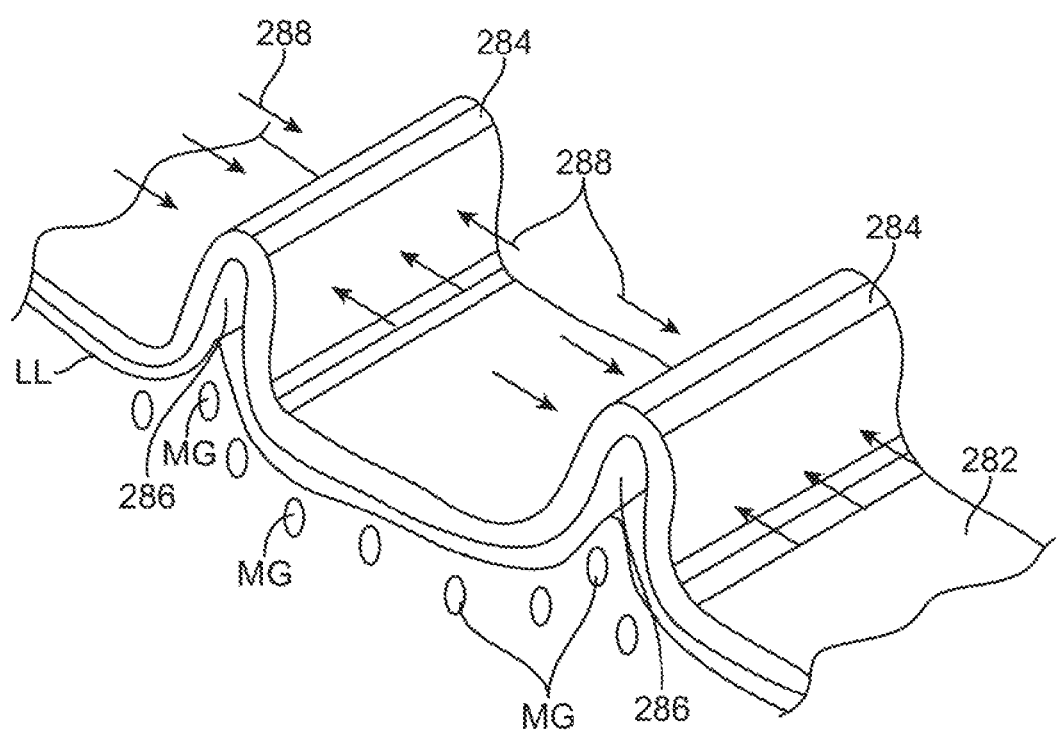
FIG. 34 shows a detail perspective view of the treatment strip of FIG. 33 illustrating an example of biasing mechanisms incorporated along the strips.

In this example, the biasing mechanism 284 may locally squeeze or compress the underlying skin to apply a pressure to the meibomian glands MG to facilitate the clearing of any obstructions, particularly if applied simultaneously with the heat treatment. An example of a biasing mechanism 284 is illustrated in the perspective view of FIG. 34 which shows how the biasing mechanism 284 may generally comprise portions of the strip 282 or separate members biased to form corresponding channels 286 which are configured to flex in an open or closed configuration. When the strip is initially placed upon the skin, the ends of the strip may be pulled to open the channels 286 which may then be placed upon the skin surface. As the strip and biasing mechanisms 284 relax, the underlying skin and meibomian glands MG may be compressed or pinched by the compression forces 288 induced into the biasing mechanism 284.

Figure 35:
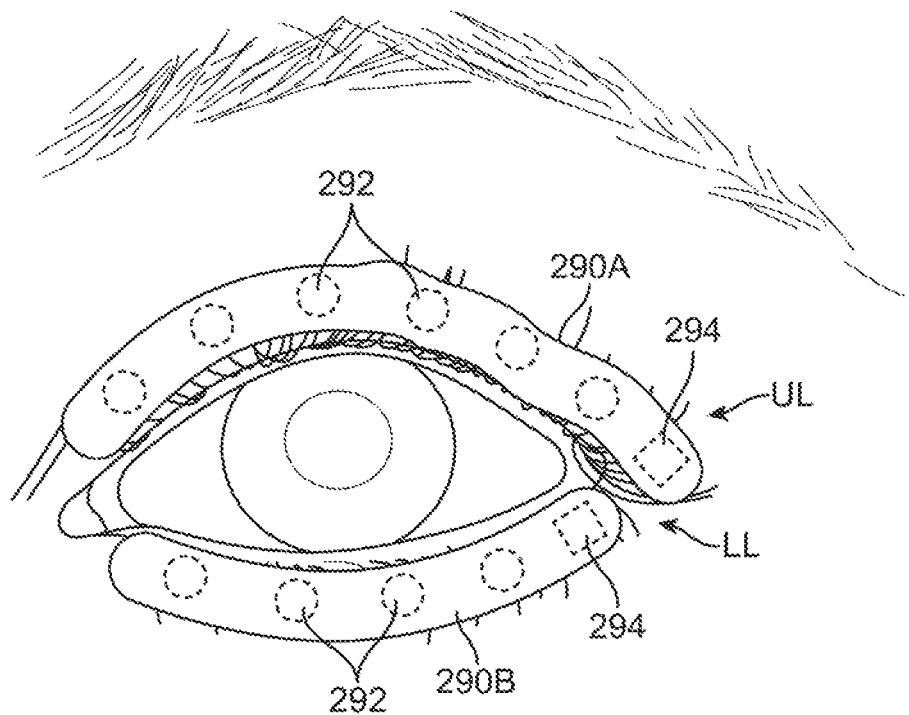
FIG. 35 shows another variation of treatment strips incorporating one or more transducers for imparting a vibrating force to the underlying tissue and meibomian glands.

Aside from a compression force, the strip may be formed with alternative components such as a mechanical component to impart vibrational energy to facilitate the expression of the meibomian glands and promote oil secretion. An example is illustrated in FIG. 35 which shows another variation of the contoured strip 290A, 290B having one or more vibrating elements 292 (e.g., piezoelectric transducers, electromagnetic actuators, eccentrically coupled rotating elements, etc.) incorporated along the strips 290A, 290B. The one or more vibrating elements 292 may be electrically coupled to a power supply and/or processor 294 also contained along the strips 290A, 290B. Moreover, the vibrational energy may be imparted separately from heat treatment or in combination with the heat therapy. The power supply may include a micro-battery which can be rechargeable to deliver microcurrents of energy.

Figure 36:
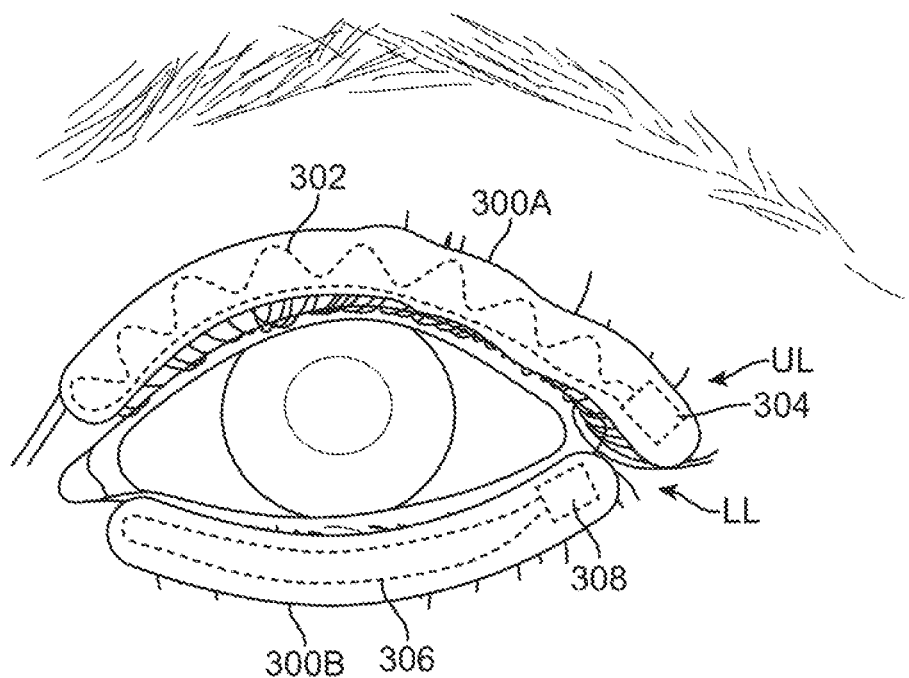
FIG. 36 shows yet another variation of treatment strips incorporating electrodes through the length of the strips.

Aside from the application of mechanical pressure or vibrational energy, other forms of energy may also be delivered by one or more of the treatment strips. Another variation is illustrated in FIG. 36 which shows an upper contoured strip 300A having a conductive element 302 such as a wire integrated along the entire length (or a partial length) of the contoured strip 300A. The conductive element 302 may be configured in an alternating pattern or it may be simply aligned along the length of the strip as shown by conductive element 306 (or electrically resistive) along the lower contoured strip 300B. Each of the conductive elements 302, 306 may be in electrical communication with a respective power supply and/or processor 304, 308. The conductive elements 302, 306 may be selectively actuated to apply either heat energy or they may configured to apply radio-frequency (RF) energy to the underlying skin and meibomian glands. With respect to the application of electrical energy, one form of electrical energy applicable by the treatment strips may include use of a transcutaneous electrical nerve stimulation feature, e.g., to deliver neural stimulation to increase tear production. The conductive elements may generate the thermal energy via various power sources, e.g., battery, solar cell, kinetic movement, RF, etc.

Figure 37:
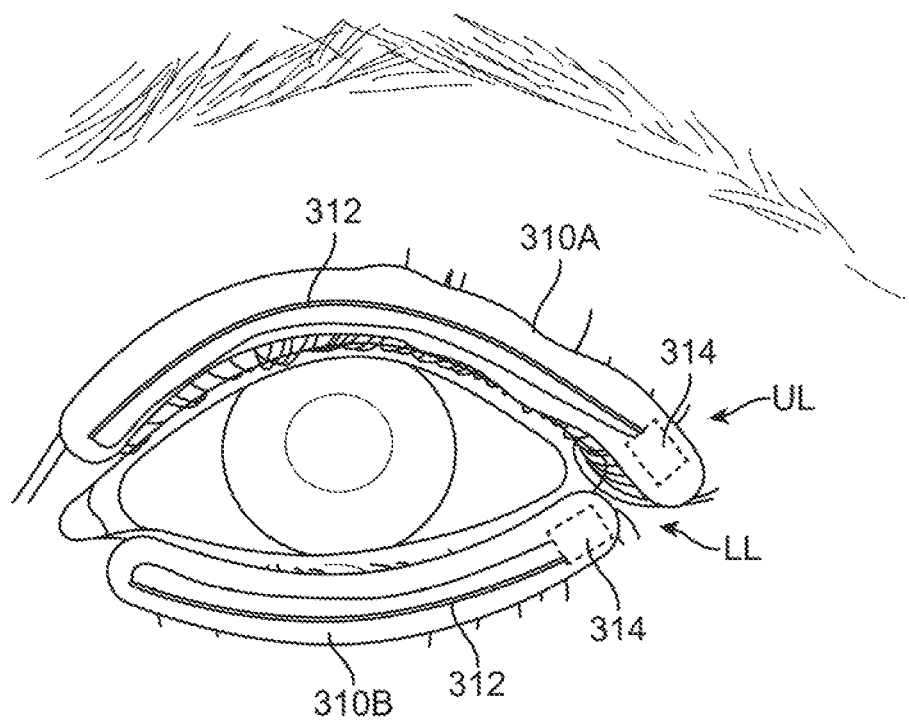
FIG. 37 shows yet another variation of treatment strips incorporating microwave antennas along the strips.
Figure 38:
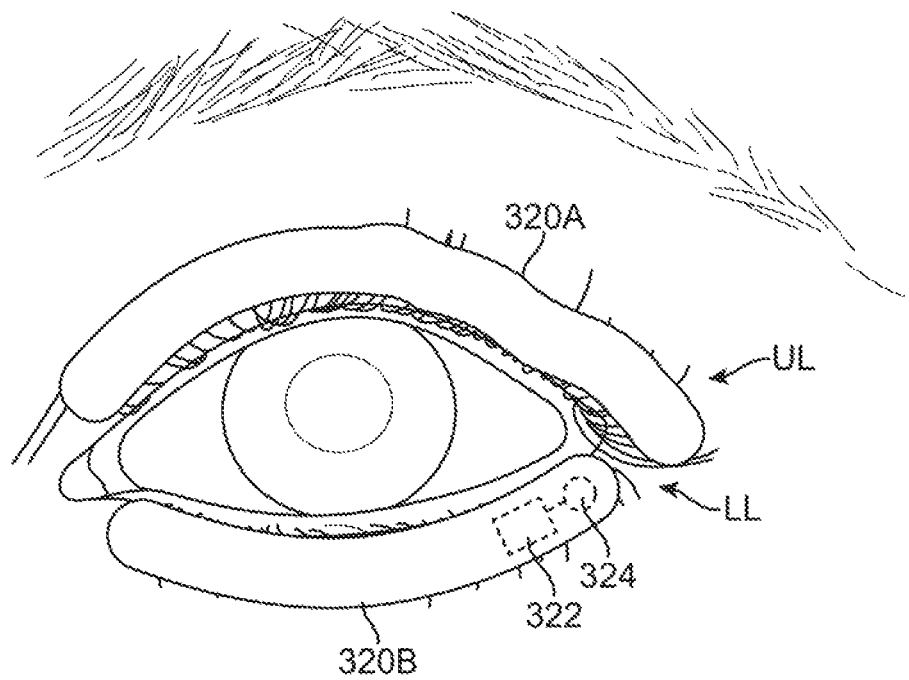
FIG. 38 shows yet another variation of a treatment strip incorporating a timer and indicating for alerting a user when a treatment has been completed.

FIG. 37 shows yet another variation where the contoured strips 310A, 310B may be configured to incorporate an electrode or antenna 312 coupled to a power supply and/or processor 314 for applying, e.g., microwave energy to the underlying meibomian glands. Aside from the electrical or microwave energy, the treatment strips may be configured to apply yet other forms of energy for treating the meibomian glands. For example, other variations may incorporate actuators or transmitters for applying ultrasonic, RF, microwave, magnetic, photonic (light energy in the infrared or visible light spectrum), etc. In yet other variations, the conductive elements may be configured to function as electromagnetic elements once actuated or the strips may incorporate ferromagnetic elements to promote closure of the eyelids. The magnetic force could serve to squeeze the meibomian glands and express the oily obstruction as the eyes are opened and re-opened when overcoming the magnetic force.

In yet another variation, one or both treatment strips 320A, 320B may be configured to incorporate an indicator 324, e.g., LED light, alarm, vibration element, etc., electrically coupled to a power supply and/or processor 322 to alert the patient when a prescribed treatment has been completed. This feature (and any of the other features) may be combined with any of the other variations of the treatment strips described herein as practicable.

With the incorporation of a processor into the treatment strips, treatment times or other parameters such as temperature of the strips may be programmed and optionally shut on or off selectively by the patient or automatically. Moreover, other parameters such as the frequency of the heat delivery or other stimulation may also be programmed by the processor to provide further flexibility in treatment.

The applications of the devices and methods discussed above are not limited to the treatment of dry eye syndrome but may include any number of further treatment applications. Moreover, such devices and methods may be applied to other treatment sites within the body where acute or chronic inflammation causes a disease or condition. The treatment strips can be accordingly custom-designed to follow the path of the underlying physiology, e.g. custom designed and contoured cooling or heating treatment strips to treat acute or chronic sinusitis, respectively, rhinitis and allergic rhinitis, etc. Modification of the above-described assemblies and methods for carrying out the invention, combinations between different variations as practicable, and variations of aspects of the invention that are obvious to those of skill in the art are intended to be within the scope of the claims.

What is claimed is:

1. A treatment assembly for dry eye syndrome, comprising:
an upper strip configured to adhere to an underlying region of skin of an upper eyelid of a subject such that the treatment assembly is configured to allow for the subject to blink naturally without restriction from the upper strip, wherein the upper strip has an upper curved or arcuate periphery which is configured to extend and follow a superior border of the meibomian glands of the upper eyelid and a lower periphery which is configured to extend and follow a free margin of the upper eyelid such that an outer boundary of the upper strip is configured to be contained by an underlying tarsal plate of the upper eyelid;
a lower strip configured to adhere to an underlying region of skin of a lower eyelid of the subject, wherein the lower strip has an upper periphery which is configured to extend and follow a free margin of the lower eyelid and a lower curved or arcuate periphery which is shaped to extend and follow an inferior border of one or more meibomian glands of the lower eyelid such that an outer boundary of the lower strip is configured to be contained by an underlying tarsal plate of the lower eyelid; and
a controller in communication with the upper and lower strips, wherein the controller is programmed to control one or more parameters of the treatment assembly, wherein the one or more parameters include at least one heating parameter, wherein the upper and lower strips each has a thickness of up to 3.175 mm, wherein the upper and lower strips each further comprise a heating mechanism configured to be in thermal communication with the respective regions of skin of the upper eyelid and of the lower eyelid and is configured to emit thermal energy to the underlying regions of skin while the subject is unhindered from blinking during a heat treatment, and wherein the heating mechanism of the upper strip substantially extends the entire length of the upper strip and the heating mechanism of the lower strip substantially extends the entire length of the lower strip such that at least a portion of the heating mechanism of the upper strip is configured to follow the superior border of the meibomian glands of the upper eyelid and at least a portion of the heating mechanism of the lower strip is configured to follow the inferior border of the one or more meibomian glands of the lower eyelid.

2. The assembly of claim 1 wherein the upper and lower strips each comprise a contact surface for placement against the regions of skin.

3. The assembly of claim 1 further comprising a thermochromic layer in thermal communication with the heating mechanism.

4. The assembly of claim 1 wherein the heating mechanism is configured to generate heat in a temperature range of about 20° to 55° C.

5. The assembly of claim 1 wherein the heating mechanism is configured to generate heat for a period of time of about 5 minutes to 24 hours.

6. The assembly of claim 1 wherein the one or more strips comprise a cooling layer in thermal communication with the region of skin.

7. The assembly of claim 6 wherein the cooling layer is configured to reduce in temperature over a range of about 0° C. to 37° C.

8. The assembly of claim 6 wherein the cooling layer comprises a hydrogel layer.

9. The assembly of claim 1 wherein the upper and lower strips each comprise an insulative layer.

10. The assembly of claim 1 wherein the upper and lower strips each has a length ranging from about 1 mm to 50 mm.

11. The assembly of claim 1 wherein the upper and log er strips each has a width ranging from about 1 mm to 25 mm.

12. The assembly of claim 1 wherein the controller is attached to the upper and lower strips.

13. The assembly of claim 1 wherein the one or more parameters comprise a temperature, treatment time, frequency of treatment, or thermal profile of the upper or lower strips.

14. The assembly of claim 1 further comprising one or more additional strips configured to adhere to a second region of skin in proximity to a lacrimal gland of the subject.

15. The assembly of claim 1 further comprising one or more biasing mechanisms positioned along the upper or lower strips, where the one or more biasing mechanisms are configured to apply a pressure to the underlying regions of skin.

16. The assembly of claim 1 further comprising one or more actuators positioned along the upper or lower strips, wherein the one or more actuators are configured to impart a mechanical vibration to the underlying regions of skin.

17. The assembly of claim 1 further comprising an electrically conductive or resistive element positioned along the upper or lower strips.

18. The assembly of claim 17 wherein the electrically conductive or resistive element comprises an electrode.

19. The assembly of claim 17 wherein the electrical conductive or resistive element comprises a microwave antenna.

20. The assembly of claim 1 further comprising air indicator positioned along the upper or lower strips.

21. The assembly of claim 20 wherein the indicator comprises an auditory or visual alarm for alerting the subject.

22. The assembly of claim 1 further comprising one or more pharmaceutical, biological, or chemical agents infused within or along the upper or lower strips.

23. The assembly of claim 1 further comprising a power supply positioned along the upper or lower strips.

24. The assembly of claim 23 wherein the power supply is rechargeable.

25. The assembly of claim 1 wherein the upper and lower strips each comprise an adhesive contact layer and an outer insulative layer.

26. The assembly of claim 1 wherein a width of the upper and lower strips is 25 mm or less.

27. The assembly of claim 1 wherein a length of the upper and lower strips is 50 mm or less.

28. The assembly of claim 1 further comprising one or more thermocouples or thermistors incorporated into the treatment assembly.

29. A method of treating dry eye syndrome, comprising:
adhering an upper strip to an upper eyelid of a subject such that an upper curved or arcuate periphery of the upper strip extends and follows a superior border of the meibomian glands of the upper eyelid and a lower periphery extends and follows a free margin of the upper eyelid such that an outer boundary of the upper strip is contained by an underlying tarsal plate, and wherein the treatment assembly is configured to allow for the subject to blink naturally without restriction from the upper strip;

adhering a lower strip to a lower eyelid of the subject such that an upper periphery extends and follows a free margin of the lower eyelid and a lower curved or arcuate periphery extends and follows an inferior border of one or more meibomian glands of the lower eyelid such that an outer boundary of the lower strip is contained by an underlying tarsal plate;

applying thermal energy from a heating mechanism in the upper and lower strips to the underlying regions of skin such that the upper and lower strips emit thermal energy to the regions of skin while under control of a controller which is in communication with the upper and lower strips, wherein the controller is programmed to control one or more parameters of the treatment assembly, wherein the one or more parameters include at least one heating parameter, and wherein the heating mechanism of the upper strip substantially extends the entire length of the upper strip and the heating mechanism of the lower strip substantially extends the entire length of the lower strip such that at least a portion of the heating mechanism of the upper strip is configured to follow the superior border of the meibomian glands of the upper eyelid and at least a portion of the heating mechanism of the lower strip is configured to follow the inferior border of one or more meibomian glands of the lower eyelid;

maintaining the upper and lower strips upon the regions of skin until obstructions within the one or more meibomian glands are melted or liquefied at least partially; and clearing the obstructions at least partially by maintaining natural blinking by the subject while maintaining the upper and lower strips upon the regions of skin, wherein the upper and lower strips each has a thickness of up to 3.175 nm.

30. The method of claim 29 wherein adhering the upper snip comprises placing a contact surface of the one or more strips against the upper eyelid.

31. The method of claim 29 further comprising indicating a temperature change in the upper and lower strips via a thermochromic layer in thermal communication with the heating mechanism.

32. The method of claim 29 wherein applying thermal energy from the heating mechanism comprises increasing a temperature of the one or more strips to a temperature range of about 20° to 55° C.

33. The method of claim 29 wherein applying thermal energy from the heating mechanism comprises applying the thermal energy for a period of time of about 5 minutes to 24 hours.

34. The method of claim 29 wherein emitting energy comprises drawing thermal energy from the underlying region of skin via a cooling layer in the upper and lower strips.

35. The method of claim 34 wherein drawing thermal energy comprises cooling the cooling layer to a temperature range of about 0° C. to 37° C.

36. The method of claim 29 wherein the upper and lower strips each has a length ranging from about 1 mm to 50 mm.

37. The method of claim 29 wherein the upper and lower strips each has a width ranging from about 1 mm to 25 mm.

38. The method of claim 29 wherein the controller is attached to the upper or lower strips.

39. The method of claim 29 wherein the one or more parameters of the treatment assembly comprise temperature, treatment time, frequency of treatment, or thermal profile of the upper and lower strips.

40. The method of claim 29 further comprising adhering one or more additional strips to a second region of skin in proximity to a lacrimal gland of the subject.

41. The method of claim 29 further comprising applying a pressure or force to the underlying region of skin via one or more biasing mechanisms positioned along the upper or lower strips.

42. The method of claim 29 further comprising imparting a mechanical vibration to the underlying region of skin.

43. The method of claim 29 further comprising applying an electrical force or electrical stimulation to the underlying region of skin.

44. The method of claim 29 further comprising alerting the subject via an indicator positioned along the upper or lower strips.

45. The method of claim 29 further comprising applying one or more pharmaceutical, biological, or chemical agents to the underlying skin via the upper or lower strips.

46. The method of claim 29 wherein the method of treating dry eye syndrome further comprises treating meibomitis, blepharitis, anterior blepharitis, posterior blepharitis, or ocular rosacea.

47. The method of claim 29 further comprising stimulating the subject to facilitate blinking, triggering a blink, or maintaining longer closure during a blink.

48. The method of claim 29 further comprising monitoring a temperature of the treatment assembly via one or more thermocouples or thermistors.

49. A treatment assembly, comprising:
an upper strip configured to adhere to an underlying region of skin of an upper eyelid of a subject such that the treatment assembly is configured to allow ibr the subject to blink naturally without restriction from the upper strip, wherein the upper strip has an upper curved or arcuate periphery which is configured to extend and follow a superior border of the meibomian glands of the upper eyelid and a lower periphery which is configured to extend and follow a free margin of the upper eyelid such that an outer boundary of the upper strip is contained by an underlying tarsal plate;

a controller in communication with the upper strip, wherein the controller is programmed to control one or more parameters of the treatment assembly, wherein the one or more parameters include at least one heating parameter, wherein the upper strip has a thickness of up to 3.175 mm, wherein the upper strip further comprises a heating mechanism configured to be in thermal communication with the region of skin and is configured to emit thermal energy to the underlying region of skin while the subject is unhindered from blinking during a heat treatment, and wherein the heating mechanism substantially extends the entire length of the upper strip such that at least a portion of the heating mechanism is configured to follow the superior border of the meibomian glands of the upper eyelid.

50. The assembly of claim 49 wherein the upper strip comprises a contact surface for placement against the region of skin.

51. The assembly of claim 49 further comprising a thermochromic layer in thermal communication with the heating mechanism.

52. The assembly of claim 49 wherein the heating mechanism is configured to generate heat in a temperature range of about 20' to 55° C.

53. The assembly of claim 49 wherein the heating mechanism is configured to generate heat for a period of time of about 5 minutes to 24 hours.

54. The assembly of claim 49 wherein the upper strip comprises a cooling layer in thermal communication with the region of skin.

55. The assembly of claim 54 wherein the cooling layer is configured to reduce in temperature over a range of about 0° C. to 37° C.

56. The assembly of claim 49 wherein the upper strip comprises an insulative layer.

57. The assembly of claim 49 wherein the upper strip as a length ranging from about 1 mm to 50 mm.

58. The assembly of claim 49 wherein the upper strip has a width ranging from about 1 mm to 25 mm.

59. The assembly of claim 49 wherein the controller is attached to the upper strip.

60. The assembly of claim 49 wherein the one or more parameters comprise a temperature, treatment time, frequency of treatment, or thermal profile of the one or more strips.

61. The assembly of claim 49 further comprising an electrically conductive or resistive element positioned along the upper strip.

62. The assembly of claim 61 wherein the electrically conductive or resistive element comprises an electrode.

63. The assembly of claim 49 further comprising an indicator positioned along the upper strip.

64. The assembly of claim 63 wherein the indicator comprises an auditory or visual alarm for alerting the subject.

65. The assembly of claim 49 further comprising one or pharmaceutical, biological, or chemical agents infused within or along the upper strip.

66. The assembly of claim 49 further comprising a power supply positioned along the upper strip.

\* \* \* \* \*